US010932936B2

United States Patent
Sedghi

(10) Patent No.: US 10,932,936 B2
(45) Date of Patent: *Mar. 2, 2021

(54) SYSTEMS AND METHODS FOR WEIGHT MANAGEMENT INCLUDING VIRTUAL REALITY, ARTIFICIAL INTELLIGENCE, ACCOUNTABILITY INTEGRATION, AND BIOFEEDBACK

(71) Applicant: Appetec, Inc., Macon, GA (US)

(72) Inventor: Shahriar Sedghi, Macon, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/809,431

(22) Filed: Mar. 4, 2020

(65) Prior Publication Data

US 2020/0253769 A1    Aug. 13, 2020

Related U.S. Application Data

(63) Continuation-in-part of application No. 16/510,751, filed on Jul. 12, 2019, which is a continuation-in-part of application No. 16/276,412, filed on Feb. 14, 2019, which is a continuation-in-part of application No. 16/115,452, filed on Aug. 28, 2018, now Pat. No. 10,251,767, which is a continuation-in-part of application No. 15/893,576, filed on Feb. 9, 2018, now Pat. No. 10,166,132, which is a continuation-in-part of application No. 15/587,316, filed on May 4, 2017, now Pat. No. 9,925,081, which is a continuation-in-part of application No. 14/660,846, filed on Mar. 17, 2015, now Pat. No. 9,687,375.

(51) Int. Cl.
*A61F 5/00* (2006.01)
*A61B 5/00* (2006.01)
*G06F 3/01* (2006.01)
*A61B 17/00* (2006.01)

(52) U.S. Cl.
CPC ............ *A61F 5/0036* (2013.01); *A61B 5/486* (2013.01); *A61B 5/7435* (2013.01); *A61B 5/7455* (2013.01); *G06F 3/011* (2013.01); *A61B 2017/00876* (2013.01)

(58) Field of Classification Search
CPC ........ A61F 5/0026; A61F 5/003; A61F 5/004; A61F 5/0046; A61F 5/0069; A61F 5/0089; A61F 5/02; A61F 5/0036; A61F 5/0003; A61M 29/02; A63F 2300/8082; A61B 2090/365; G05B 2219/40131
See application file for complete search history.

(56) References Cited

U.S. PATENT DOCUMENTS

| | | | |
|---|---|---|---|
| 6,151,586 A | 11/2000 | Brown | |
| 9,687,375 B2* | 6/2017 | Sedghi | .................. A61F 5/004 |
| 9,925,081 B2* | 3/2018 | Sedghi | .................. A61F 5/0089 |
| 10,166,132 B2* | 1/2019 | Sedghi | .................. A61B 1/2736 |
| 10,251,767 B1* | 4/2019 | Sedghi | .................. A61F 5/004 |

(Continued)

*Primary Examiner* — Jocelin C Tanner
(74) *Attorney, Agent, or Firm* — Select Patents; Ashkon Cyrus

(57) ABSTRACT

A minimally invasive system and method for providing weight loss by inducing the feeling of satiety whereby reconditioning experiences are combined with an intragastric device that is inserted into the gastric lumen via the esophagus and an external magnetic device is used as needed to magnetically attract the intragastric device towards the inner wall of the stomach.

13 Claims, 33 Drawing Sheets

(56) References Cited

U.S. PATENT DOCUMENTS

| | | |
|---|---|---|
| 10,262,290 B1 | 4/2019 | Mossoba et al. |
| 10,265,627 B2 | 4/2019 | Ghanchi |
| 2015/0306340 A1* | 10/2015 | Giap ..................... G16H 20/40 600/301 |
| 2019/0336314 A1* | 11/2019 | Sedghi .................... A61F 5/003 |

* cited by examiner

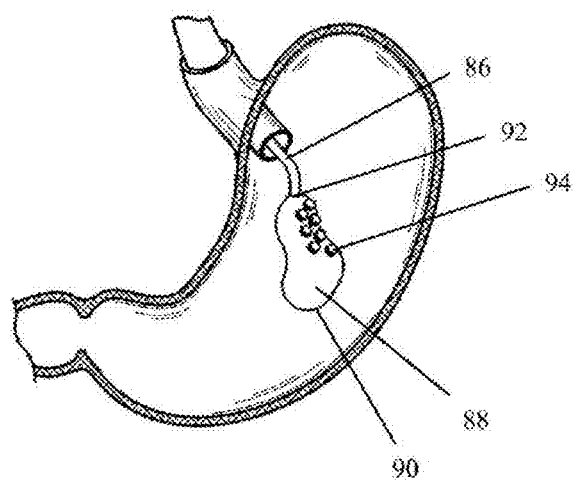
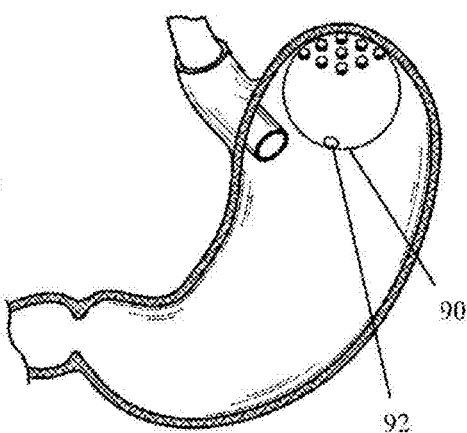
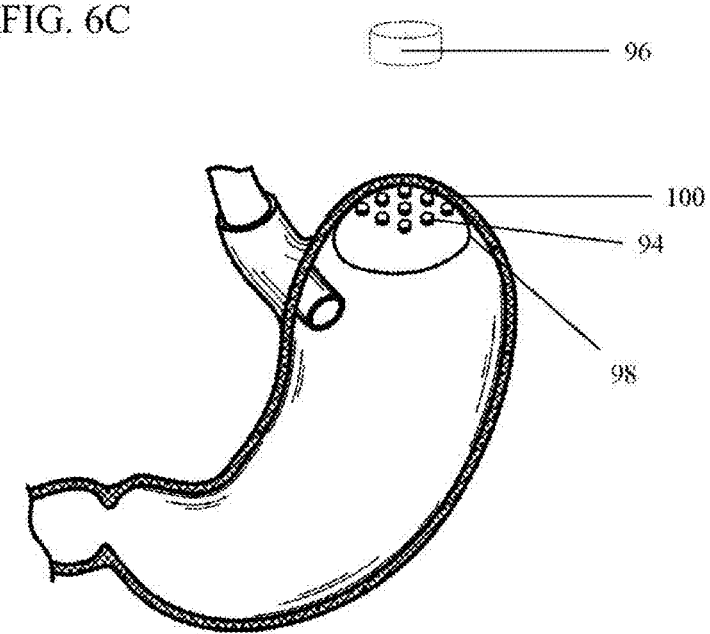

FIG. 7A
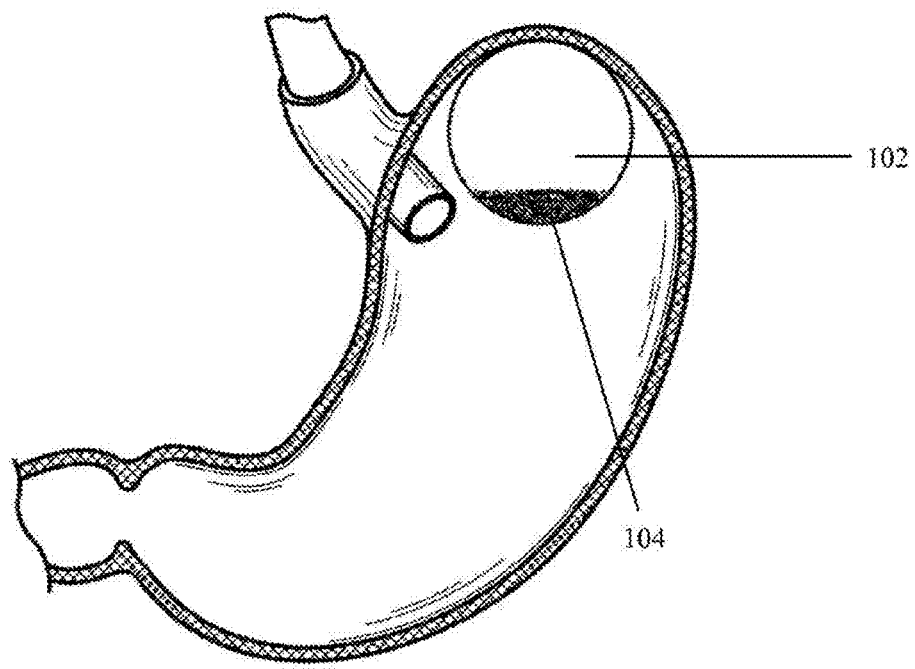
FIG. 7B
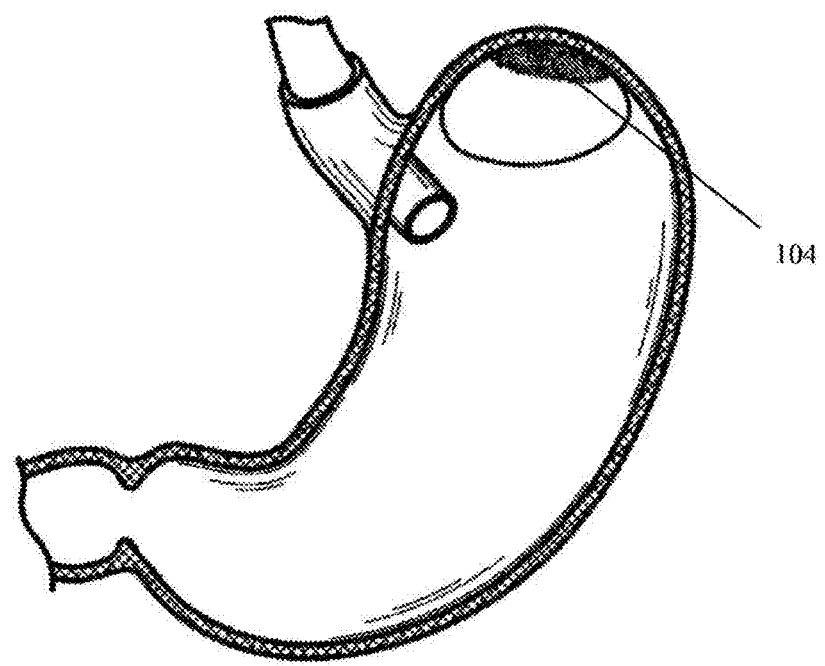

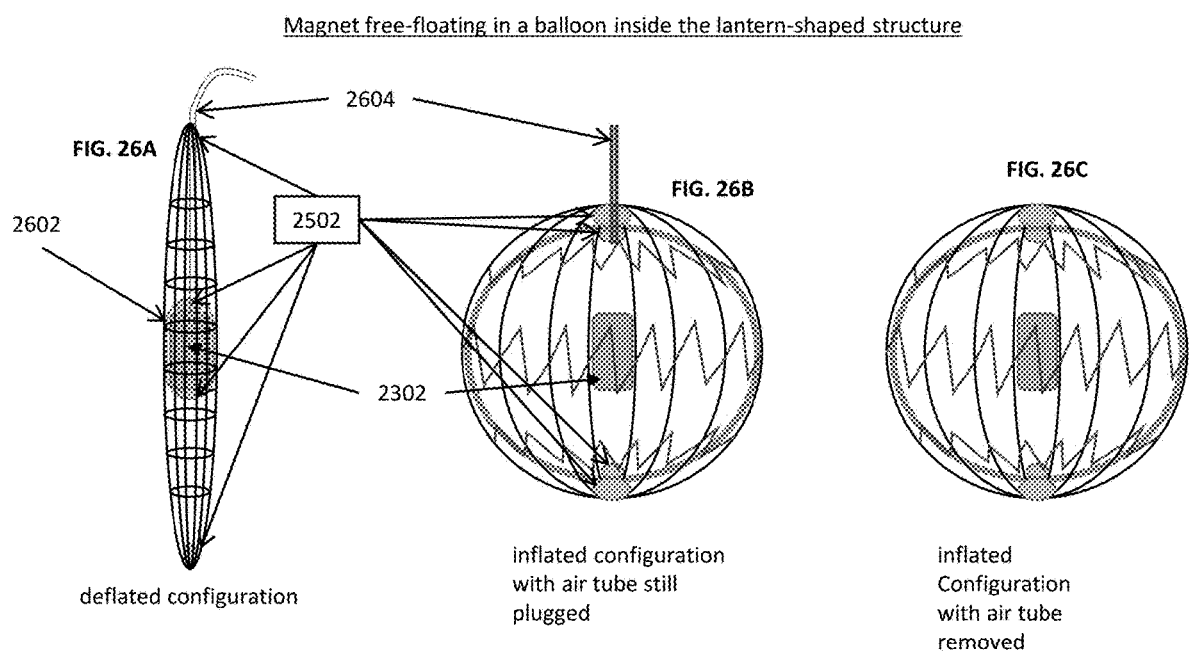

Delivery method for a magnet free floating in a lantern-shape stent

Delivery method (swallow) for a magnet free floating in an inflated balloon (non endoscopic)

Delivery method for a magnet free floating in an inflated balloon in a lantern structure Magnet fixed at the center of a pre-inflated, pre-sealed balloon inside the lantern-shaped structure inflated configuration after released in a stomach

SYSTEMS AND METHODS FOR WEIGHT MANAGEMENT INCLUDING VIRTUAL REALITY, ARTIFICIAL INTELLIGENCE, ACCOUNTABILITY INTEGRATION, AND BIOFEEDBACK

RELATED APPLICATIONS

This patent application is a continuation-in-part of Ser. No. 16/510,751, filed Jul. 12, 2019, which is a continuation-in-part of Ser. No. 16/276,412, filed Feb. 14, 2019, which is a continuation-in-part of U.S. patent application Ser. No. 16/115,452, filed on Aug. 28, 2018, which is a continuation in part of U.S. patent application Ser. No. 15/893,576 filed on Feb. 9, 2018, which is a continuation-in-part of U.S. patent application Ser. No. 15/587,316, which was filed on May 4, 2017, which is a continuation-in-part of U.S. patent application Ser. No. 14/660,846, filed on Mar. 17, 2015.

FIELD OF THE INVENTION

The present disclosure relates to obesity treatment generally and, more particularly, to systems and methods for Weight Management including Virtual Reality, Artificial Intelligence, Accountability Integration, and Biofeedback.

DESCRIPTION OF RELATED ART

Obesity is a major medical problem affecting millions of people. It is generally considered that obesity is a food addiction problem.

Obese patients currently undergo several types of invasive surgery to either staple or tie off portions of the stomach, small intestine, and/or bypass portions of the same. The goal is to reduce the amount of food desired by the patient. Current methods for achieving these results include laparoscopic banding, surgical bypass, and gastric stapling. These methods often necessitate incisions and general anesthesia, and may cause long- or short term complications.

Less invasive endoscopic procedures are also used to assist weight loss, and have primarily focused on placement of a balloon or other space-occupying device in the patient's stomach to provide a continual feeling of fullness and consequential reduction in food intake, often in conjunction with behavioral modification programs. To accomplish these procedures, an endoscope is generally utilized to guide the space-occupying device through the patient's mouth, down the esophagus, and into the stomach before relinquishing control of the device for some 4-12 months, and endoscopically retrieving it thereafter.

While these methods may be clinically efficacious, they fail to provide long term weight loss due to the body's natural adaptation to the changes. They may also induce complications including improper positioning of devices, stretching of the intestinal tract, bowel obstruction, and stomach erosion requiring invasive intervention.

The present disclosure is the $6^{th}$ application by Appetec, Inc to address these issues is the art. Specifically, the application is directed towards modifying behavior by various methods: 1) Virtual Reality 2) Artificial Intelligence 3) Accountability Integration and 4) Biofeedback.

SUMMARY OF THE INVENTION

The present disclosure provides numerous novel intragastric magnetic devices capable of inducing the feeling of satiety from inside the stomach, as well as external magnetic devices capable of intermittently adjusting, positioning, and attracting their intragastric counterparts from outside the body. This retention of non-invasive control over an intragastric device after insertion enables patients to magnetically stimulate and even stretch a specific portion of the stomach, such as the fundus, where satiety nerves are maximal. In addition to patients who may otherwise be treated surgically as morbidly obese, the invention provides greater access to minimally invasive weight loss procedures for patients who are only moderately overweight or obese, reducing the risks associated with more invasive procedures. The present disclosure is further directed towards modifying behavior by various methods: 1) Virtual Reality 2) Artificial Intelligence 3) Accountability Integration and 4) Biofeedback.

BRIEF DESCRIPTION OF THE DRAWINGS

FIG. 6A is a perspective view of an inflatable intragastric device in the deflated state during transesophageal insertion.

FIG. 6B is a perspective view of an inflatable intragastric device in the inflated state.

FIG. 6C is a perspective view of an inflated intragastric device being attracted to an external magnetic device.

FIG. 7A is a perspective view of an inflatable intragastric device containing magnetic powder.

FIG. 7B is a perspective view of an inflated intragastric device being attracted to an external magnetic device.

11A outfitted with protruding cylindrical magnets in lieu of flush embedded disc magnets.

Figure 13:
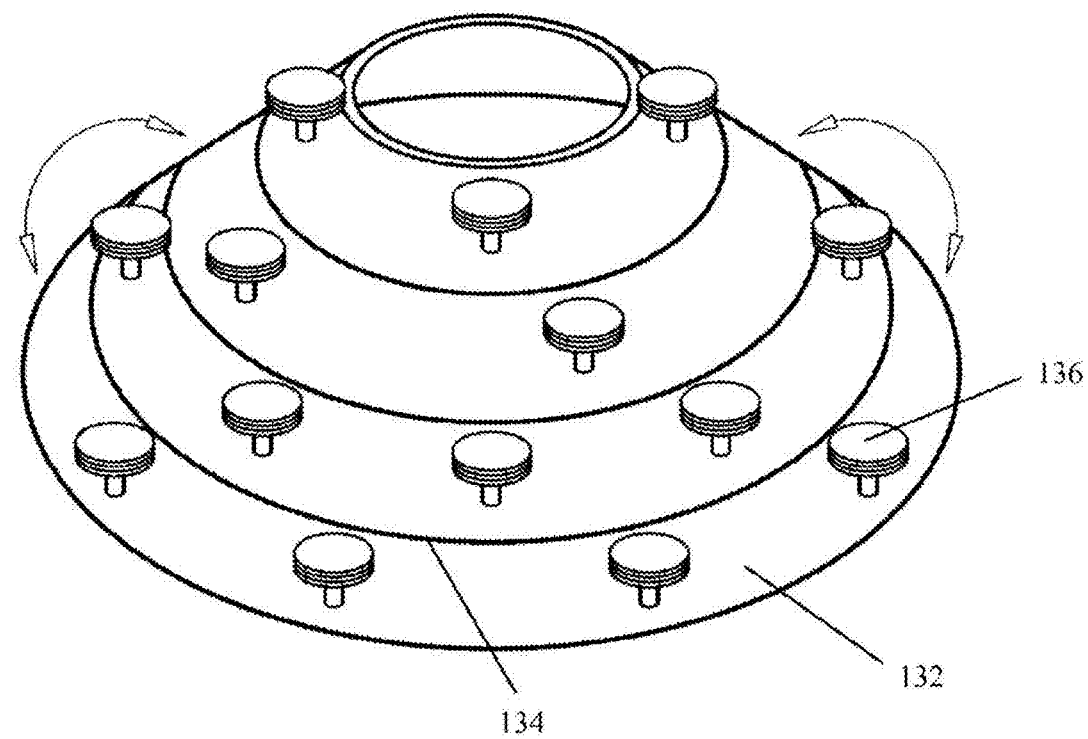

FIG. 13 is a perspective view of a collapsible frustacone-shaped intragastric device with protruding swiveling magnets.

Figure 14A:
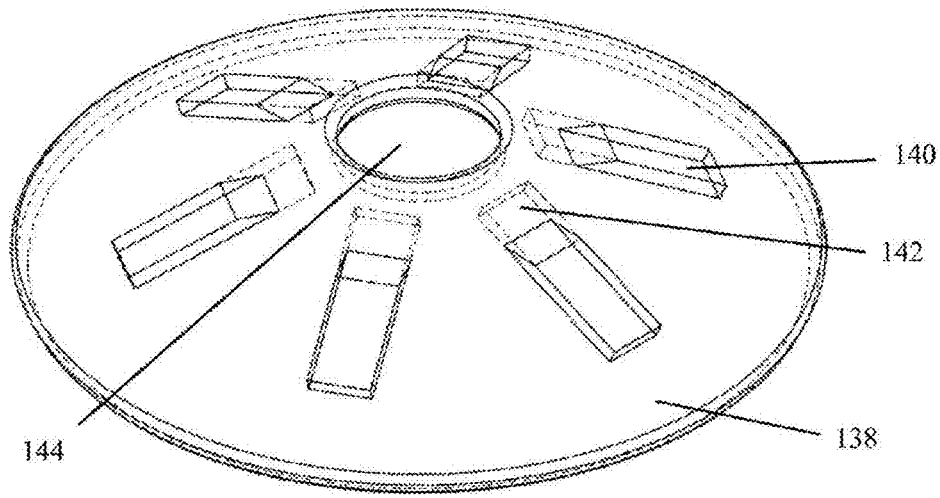
Figure 14B:
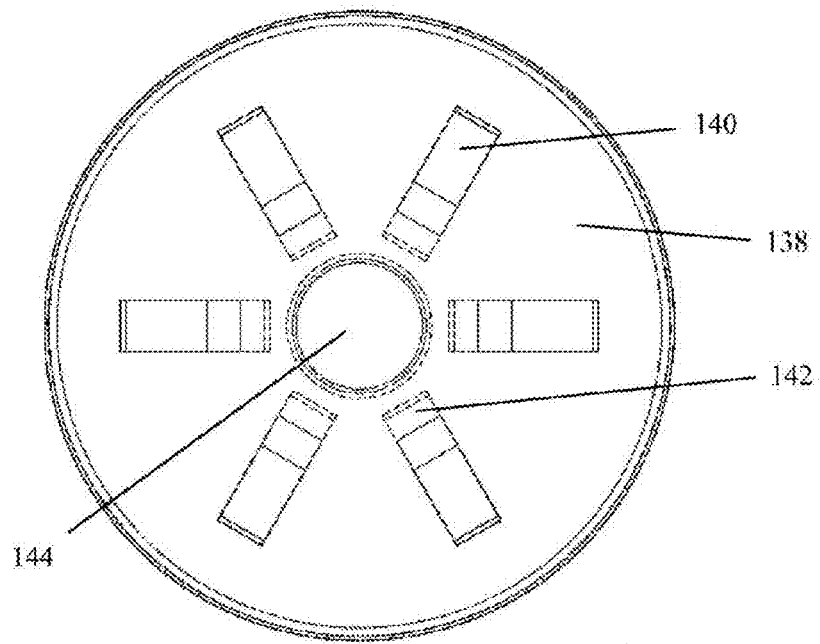
Figure 14C:
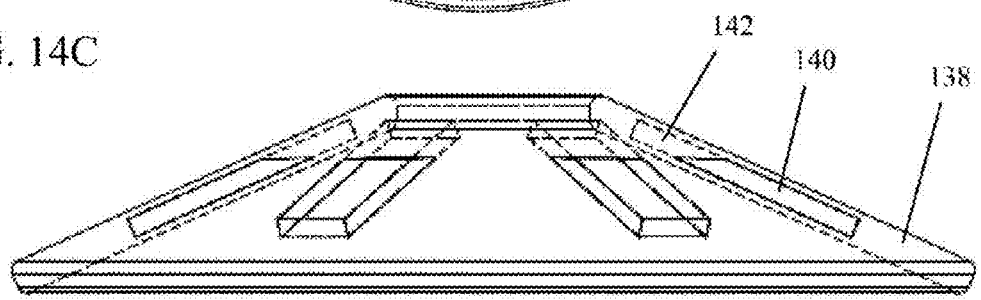

FIGS. 14A-C depict a frustacone-shaped collapsible intragastric device with embedded compartments containing magnetic powder.

Figure 15A:
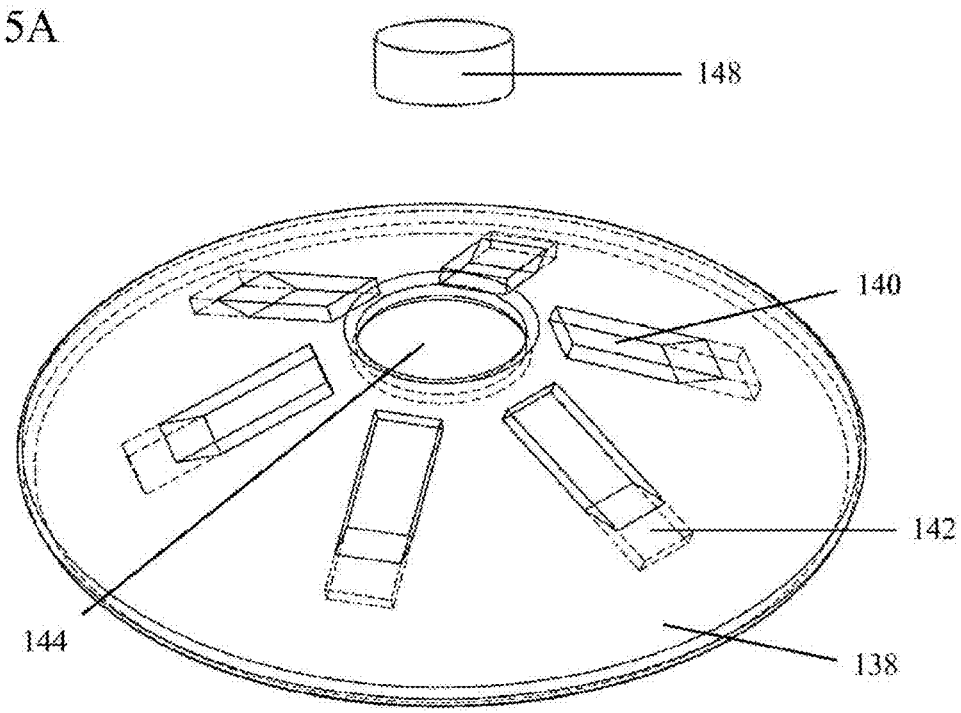
Figure 15B:
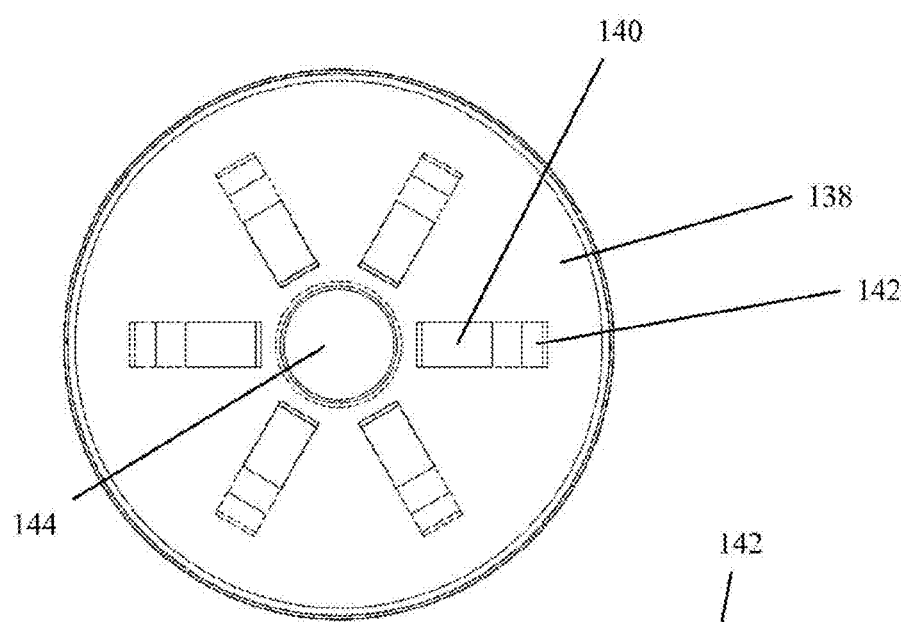
Figure 15C:
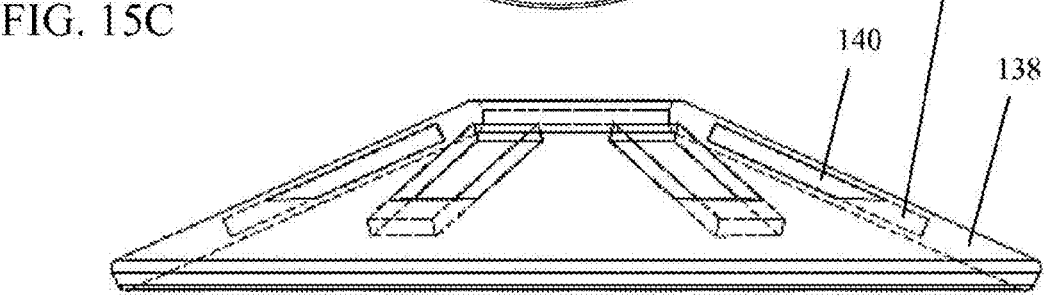

FIGS. 15A-C depict the frustacone-shaped collapsible device of FIGS. 14A-C interacting with an external device's magnetic field.

Figure 16A:
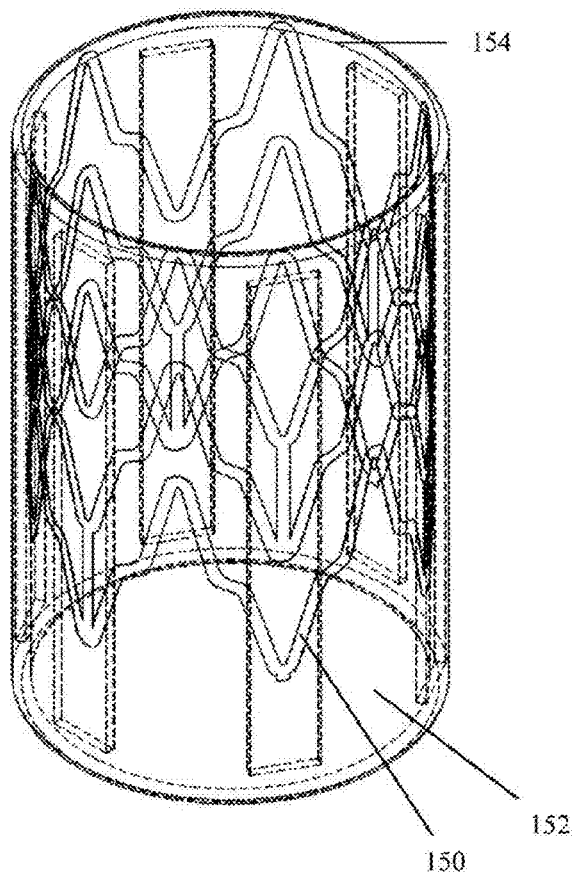
Figure 16B:
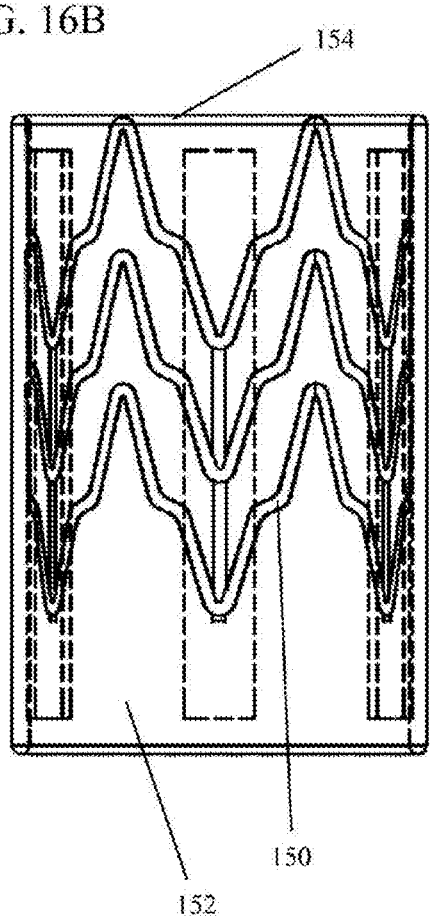
Figure 16C:
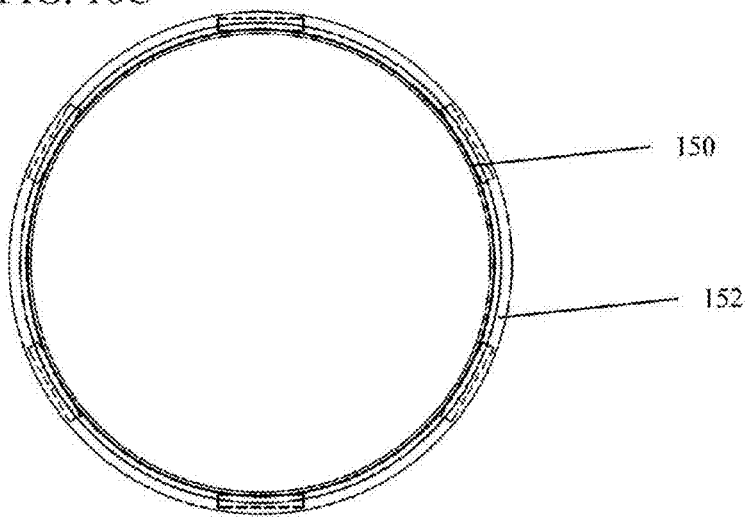

FIGS. 16A-C depict resilient mesh that can be embedded in the structure of intragastric devices.

Figure 17A:
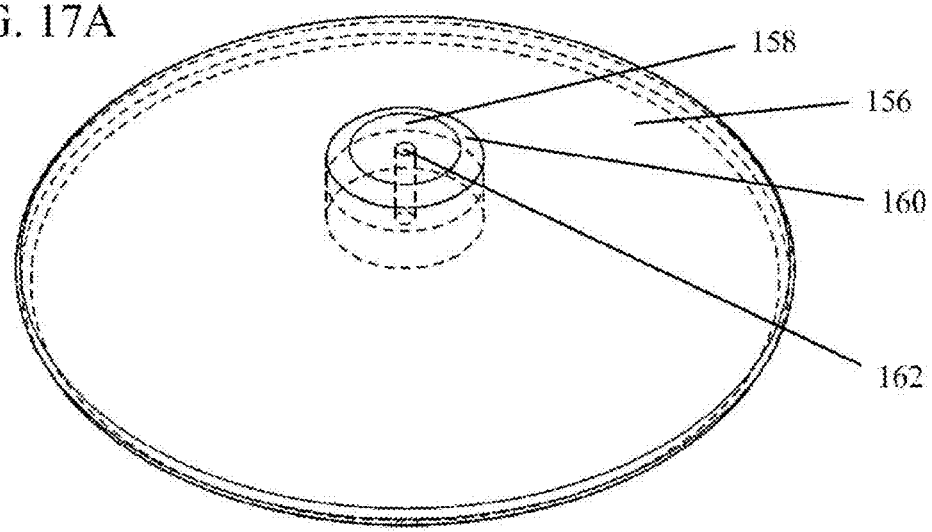
Figure 17B:
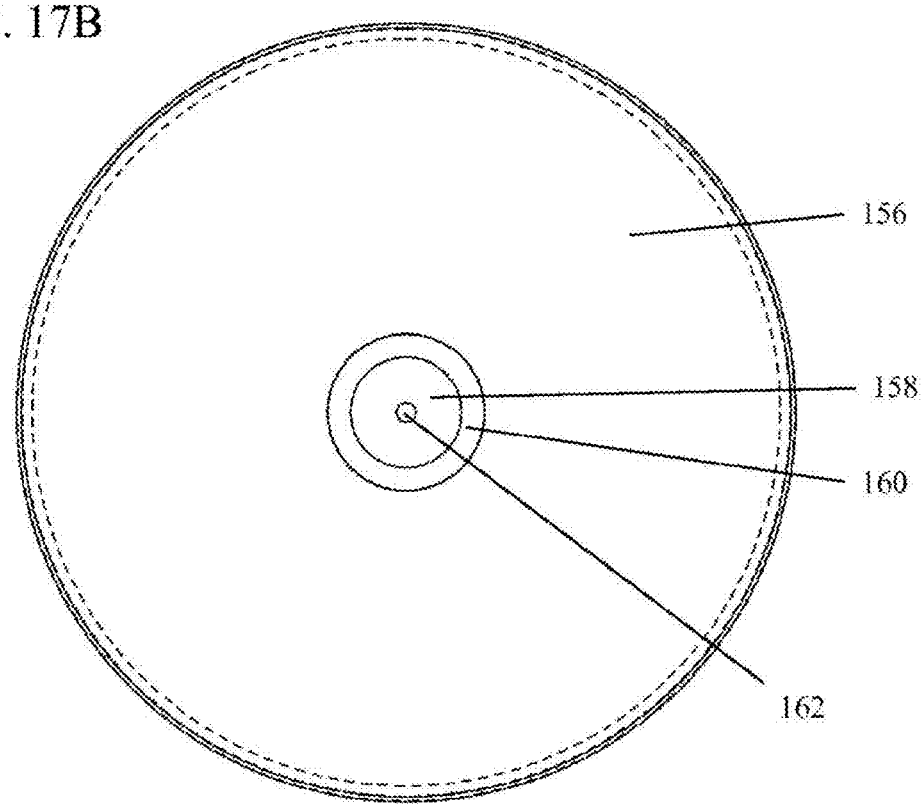
Figure 17C:
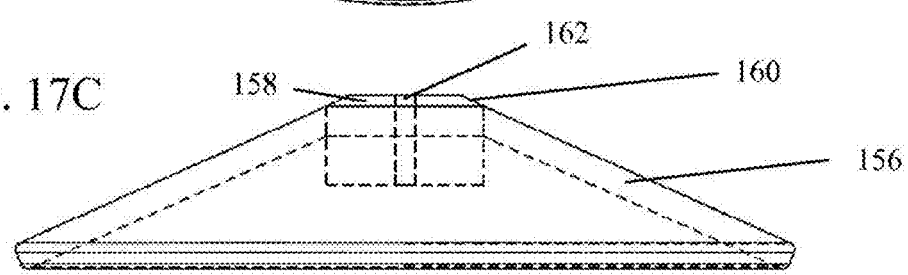

FIGS. 17A-C depict a frustacone-shaped collapsible intragastric device with a narrow central channel.

Figure 18A:
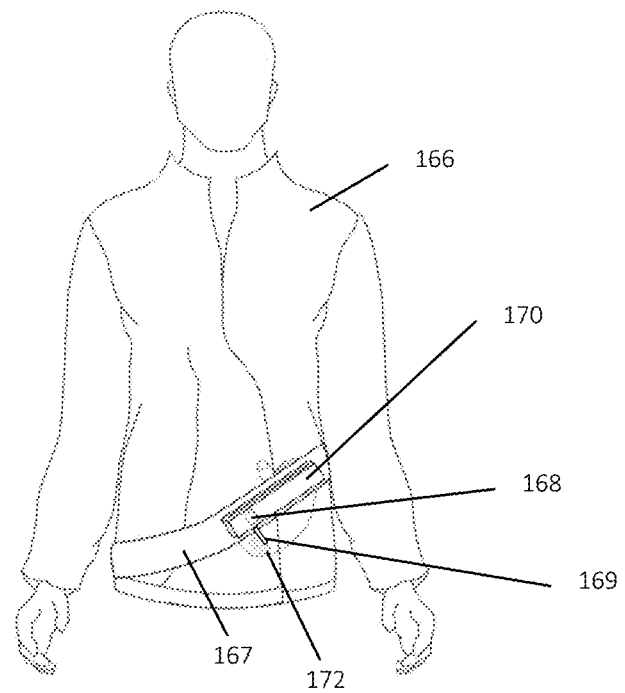

FIG. 18A is a perspective view of a belt containing an external magnetic device in the lower position.

Figure 18B:
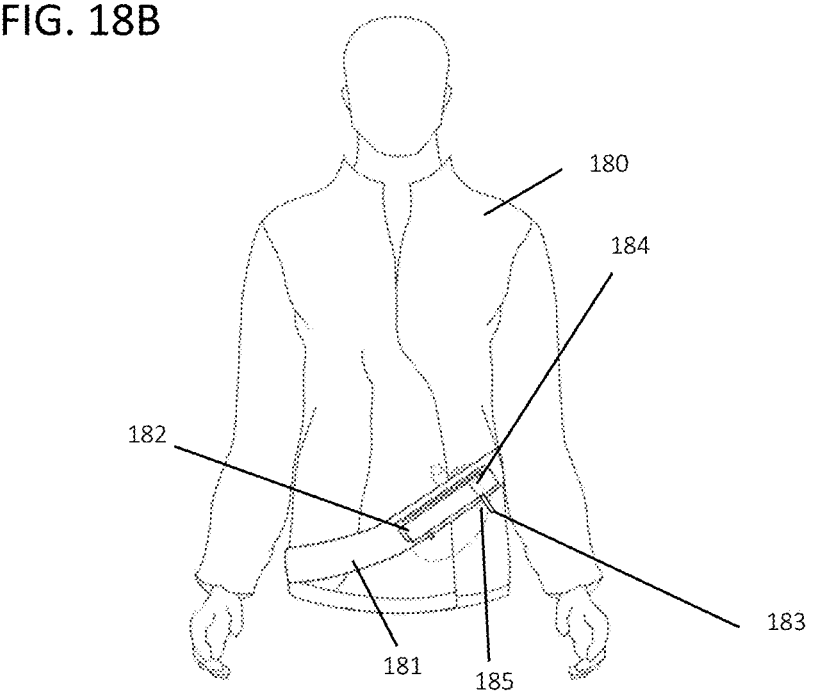

FIG. 18B is a perspective view of an belt containing an external magnetic device in the upper position.

Figure 19A:
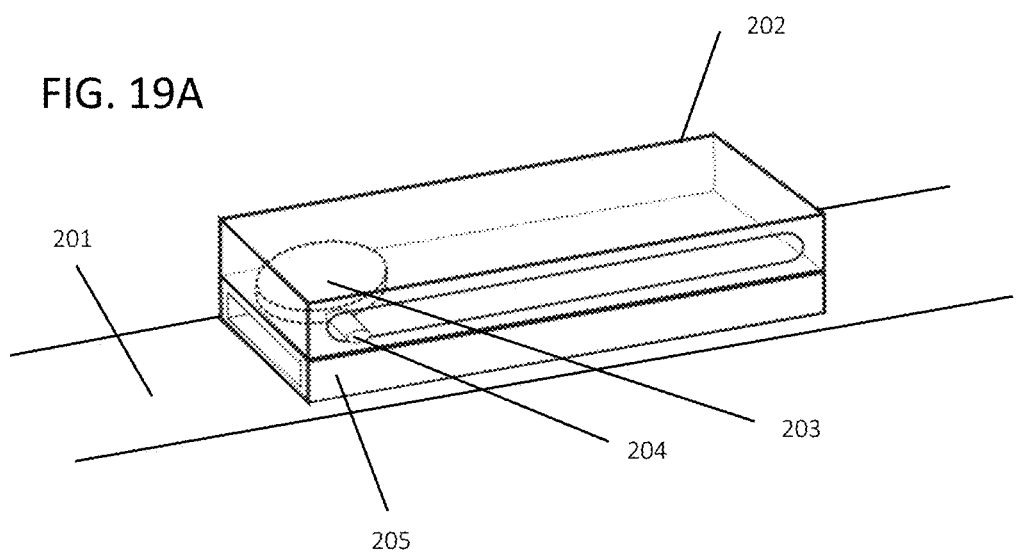

FIG. 19A illustrates an embodiment of a magnet container device.

Figure 19B:
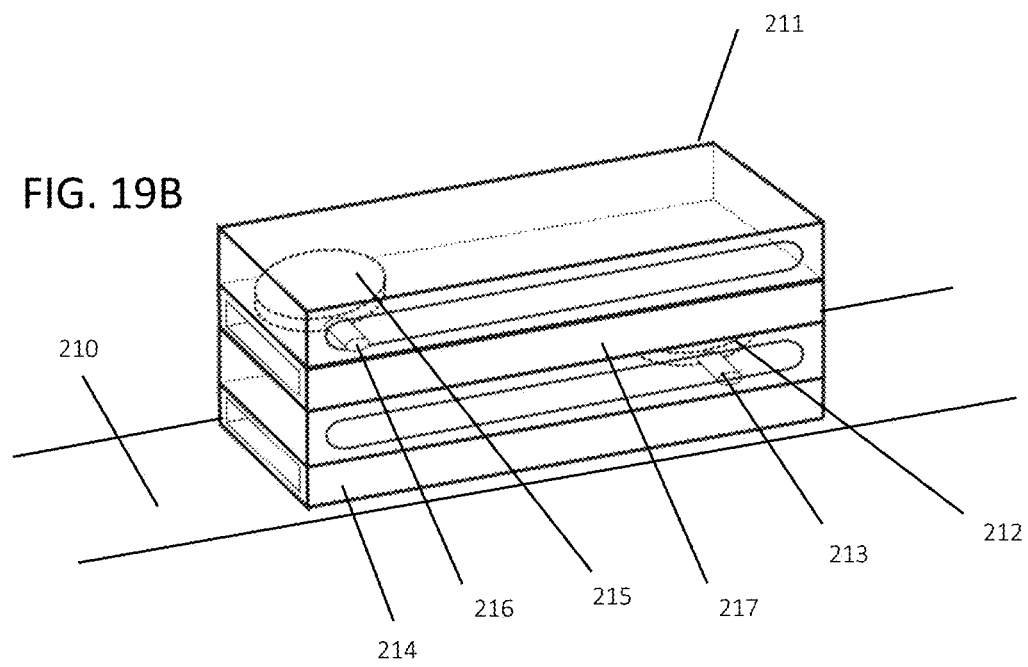

FIG. 19B is an embodiment of a magnet containing device where a second external magnet is utilized to create additional force.

Figure 20A:
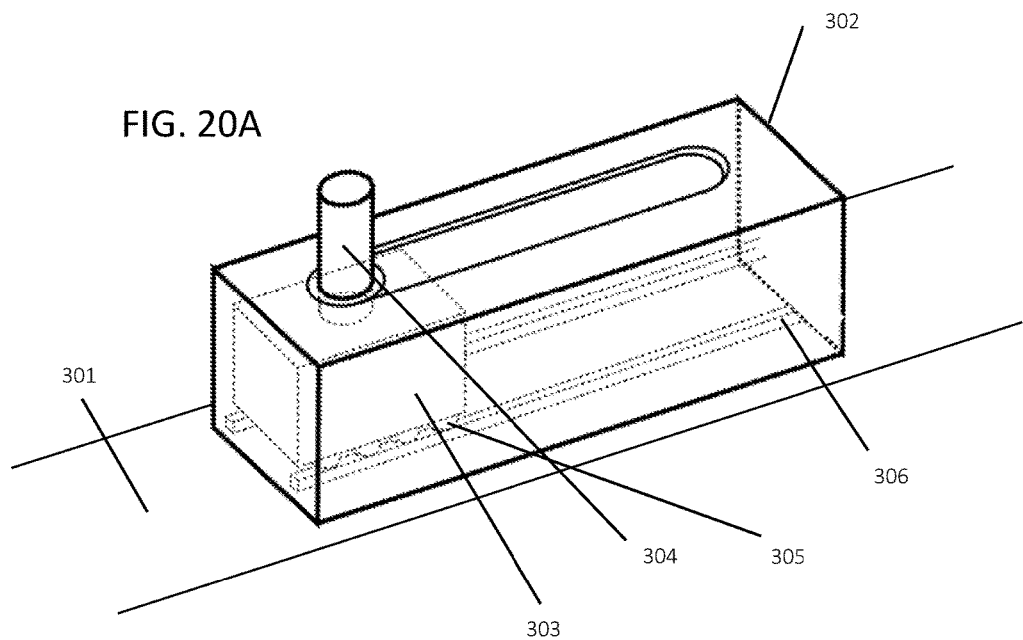

FIG. 20A illustrates an embodiment of a magnet container device which provides for moving an external magnetic device.

Figure 20B:
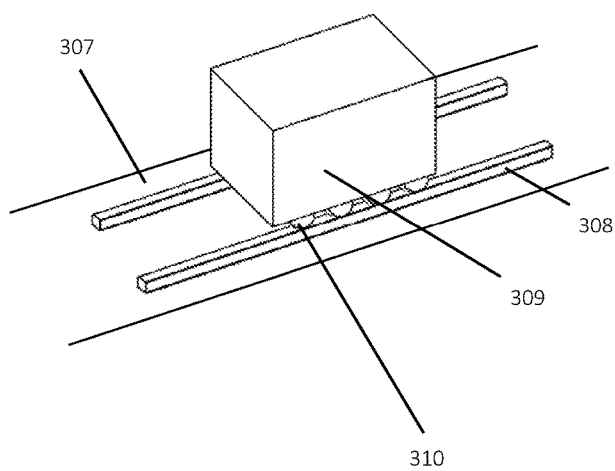

FIG. 20B illustrates a track mechanism for moving an external magnet.

Figure 20C:
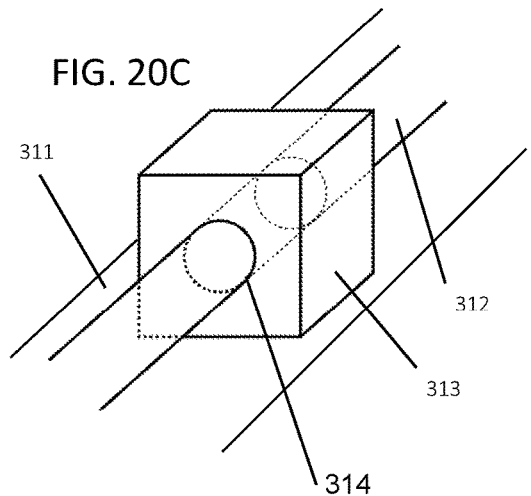

FIG. 20C illustrates a rail mechanism for moving an external magnet.

Figure 21A:
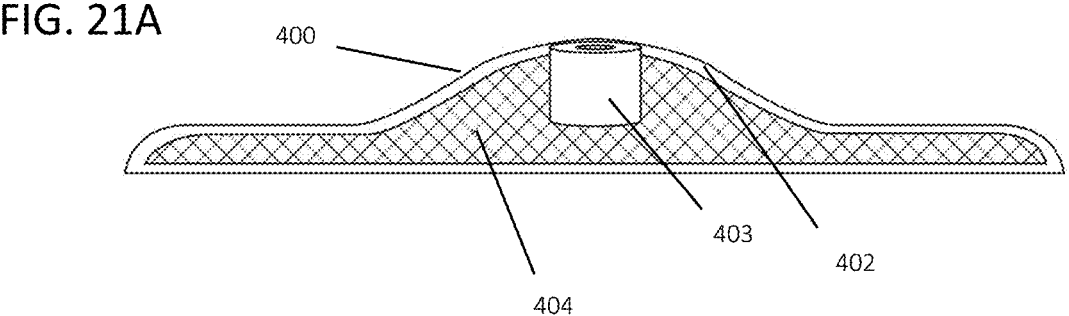

FIG. 21A illustrates a cross sectional view of an embodiment of a saucer shaped intragastric device.

Figure 21B:
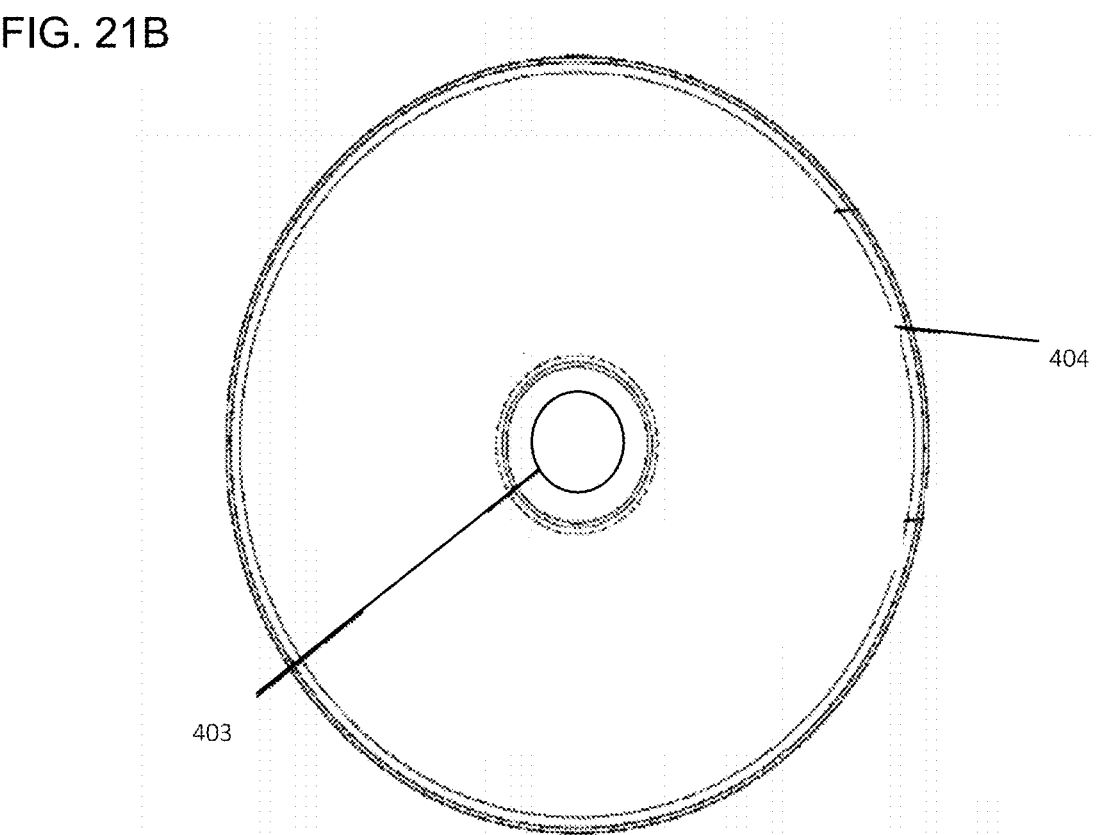

FIG. 21B is a top plan view of the intragastric device depicted in FIG. 21A.

Figure 22A:
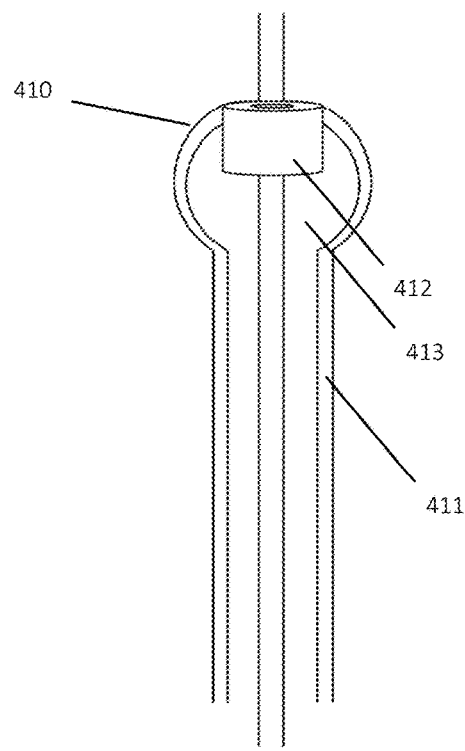

FIG. 22A illustrates a cross-sectional view of an intragastric device (410) in a collapsed state.

Figure 22B:
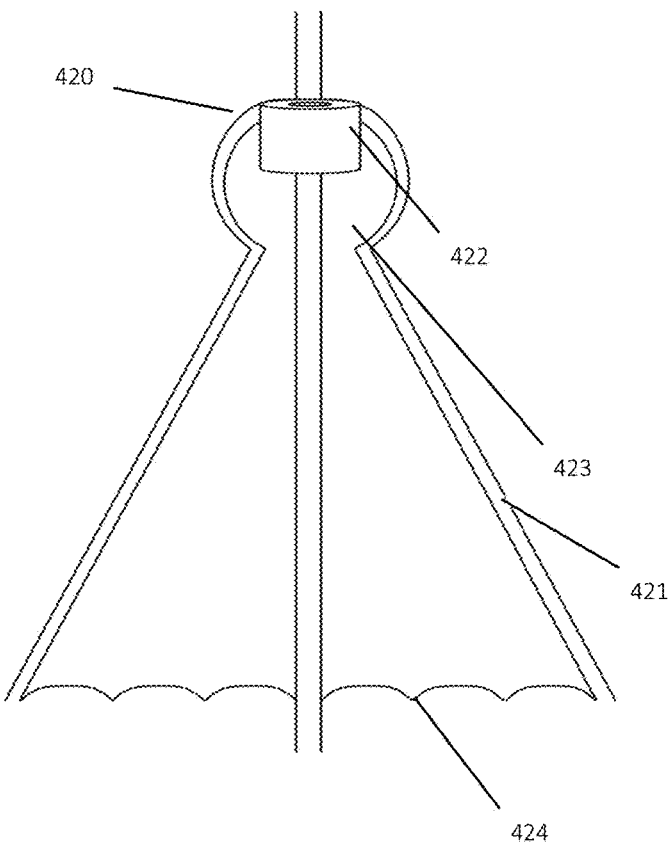

FIG. 22B illustrates a cross-sectional view of a zigzag intragastric device (420) in an expanded state.

Figure 22C:
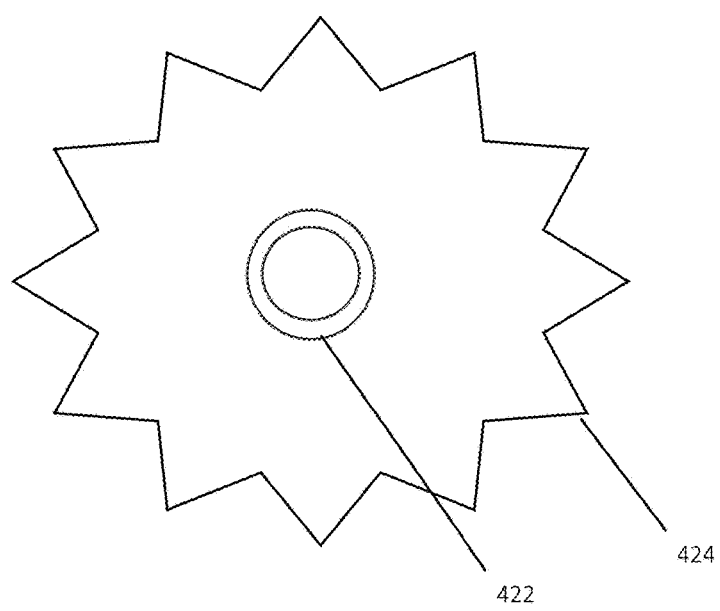

FIG. 22C is a top plan view of the zig-zag intragastric device depicted in FIG. 22B.

Figures 23A, 23B:
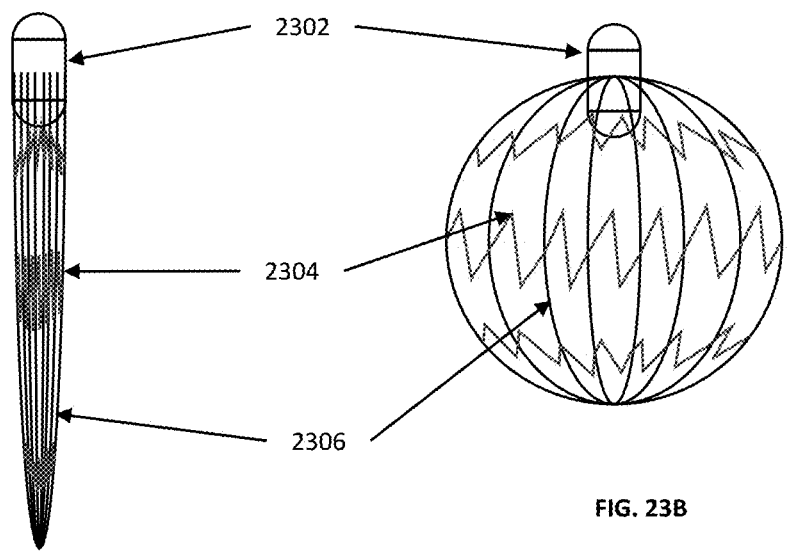

FIGS. 23A and 23B disclose an embodiment of an expandable intragastric device constructed primarily from a flexible and resilient surface resembling a "lantern" shape.

Figures 24A, 24B:
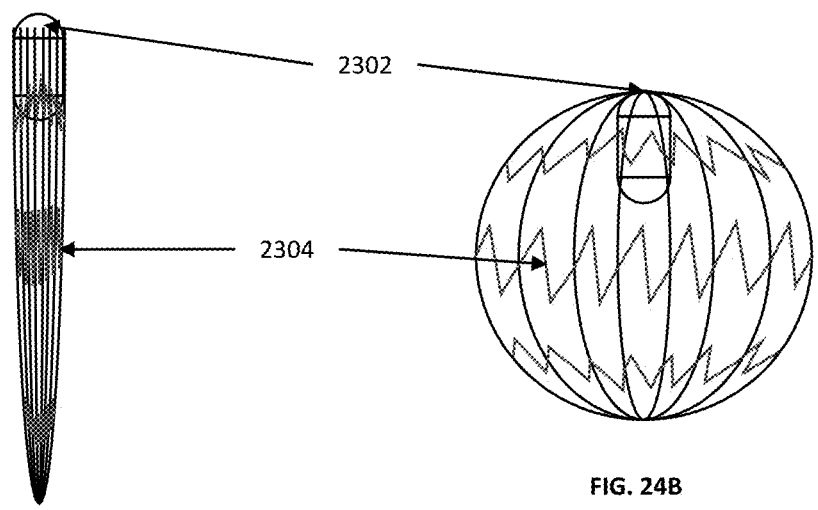

FIGS. 24A and 24B disclose an embodiment where a magnet is attached to but completely inside the lantern-shaped structure.

Figures 25A, 25B:
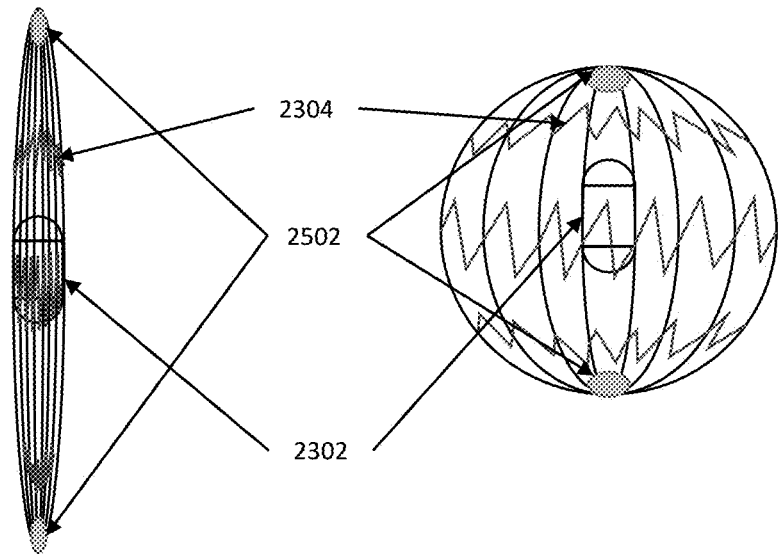

FIGS. 25A and 25B disclose an embodiment where the magnet is free-floating inside the lantern-shaped structure and contains self sealing plugs.

FIGS. 26A, 26B, and 26C disclose an embodiment where the magnet is free-floating in a balloon inside a lantern-shaped structure.

FIGS. 27-32 disclose delivery configurations for delivery a intragastric device into the stomach of a patient, either endoscopically or non-endoscopically.

Figure 33:
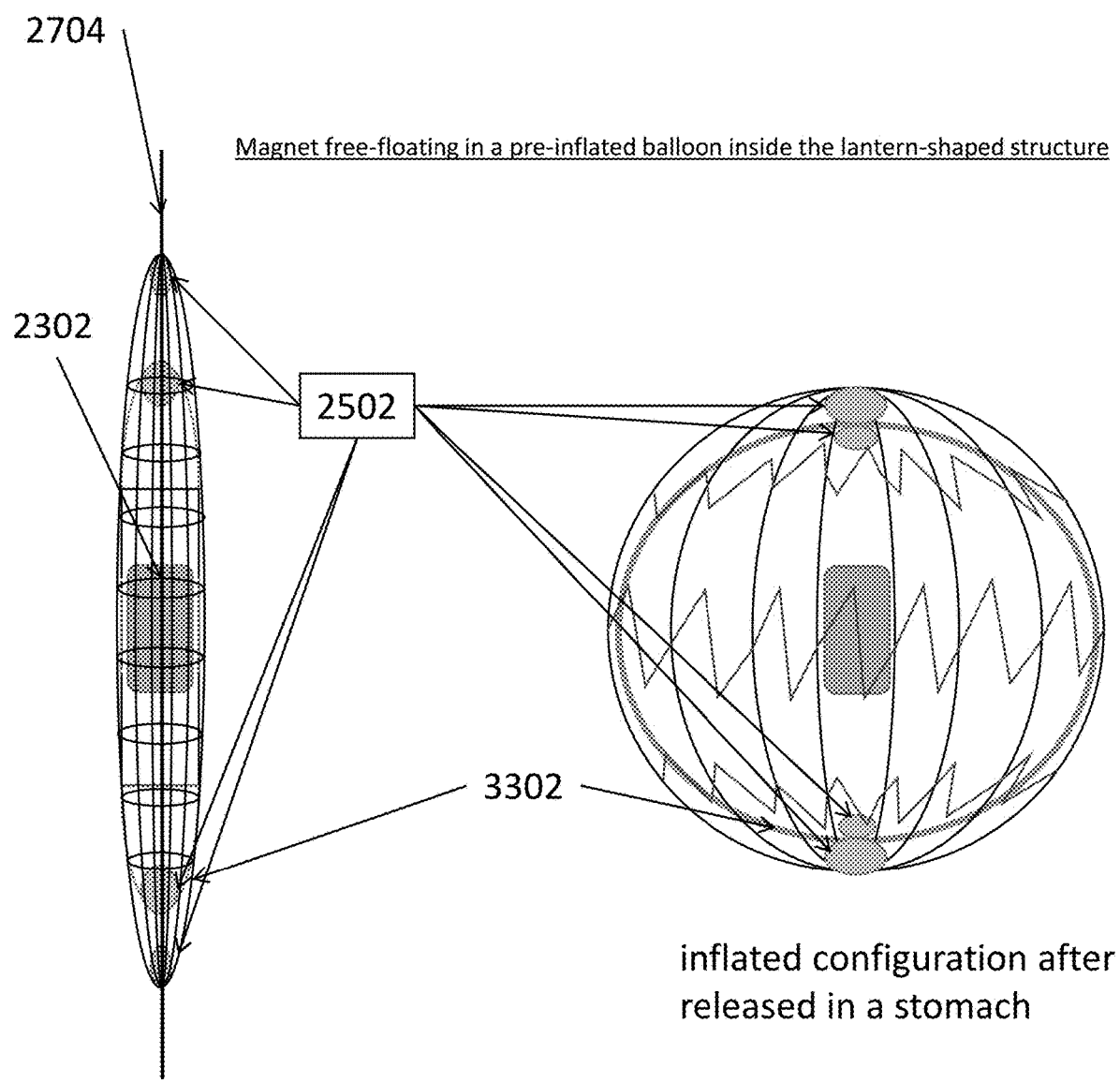

FIG. 33 discloses an alternative embodiment where a magnet is free floating in a pre-inflated balloon 3302 in a lantern structure.

Figure 34:
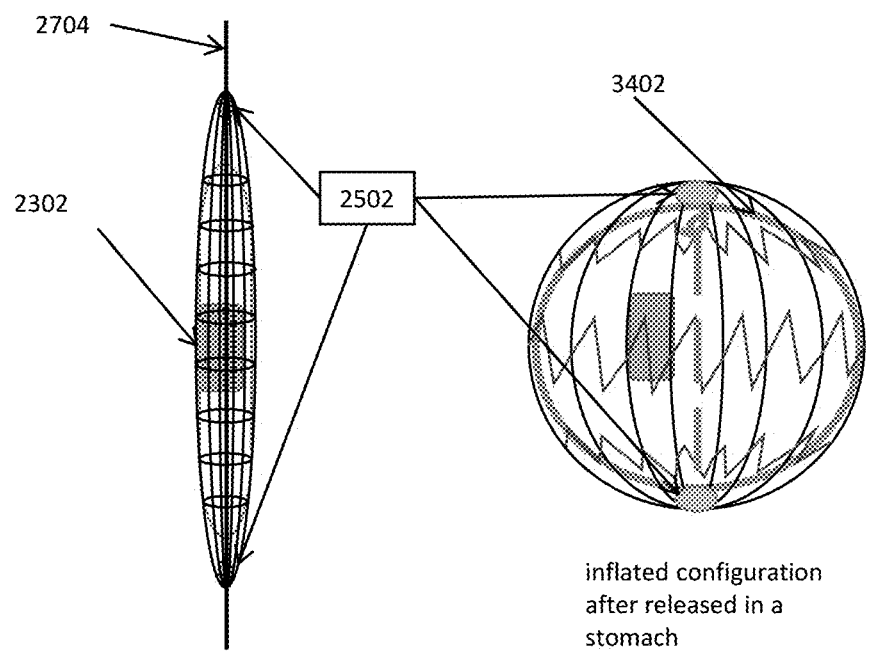

FIG. 34 discloses an alternative embodiment where a magnet is located within a pre-inflated and pre-sealed balloon of a doughnut shape with a hole through its center.

Figure 35:
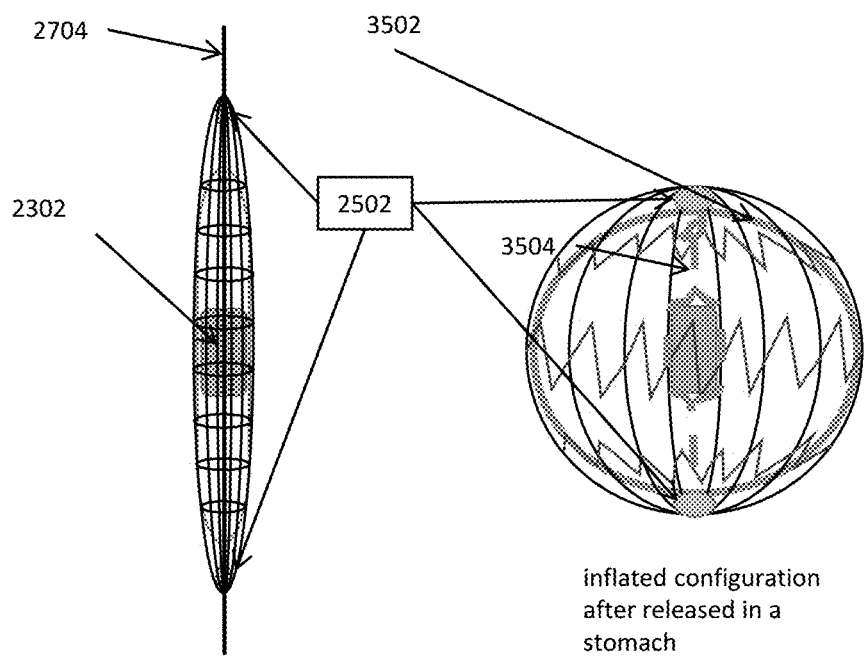

FIG. 35 discloses an alternative embodiment where a magnet is fixed at the center of a pre-inflated, pre-sealed balloon inside a lantern-shaped structure.

Figure 36A:
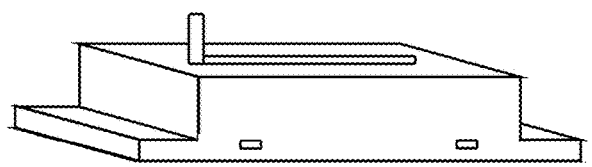

FIG. 36A discloses an external View of a magnet Compartment according to an embodiment of the invention.

Figure 36B:
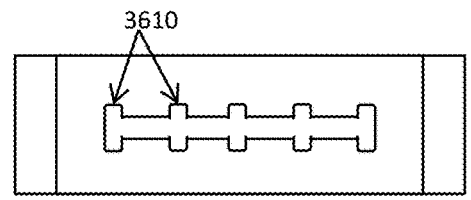

FIG. 36B discloses slots to lock the magnet's position at a fixed position.

Figure 36C:
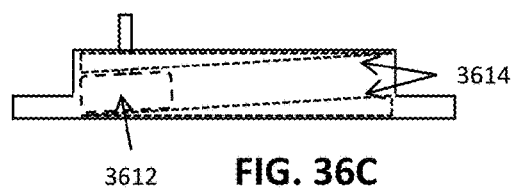

FIG. 36C discloses a side view of a magnetic compartment according to an embodiment of the invention.

Figure 37A:
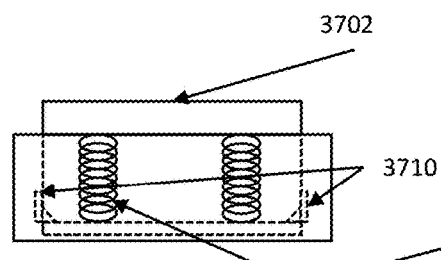

FIG. 37A discloses a short side view of a magnetic compartment in a latched configuration according to an embodiment of the invention.

Figure 37B:
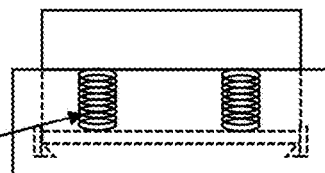

FIG. 37B discloses a short side view of a magnetic compartment in a released configuration according to an embodiment of the invention.

Figure 37C:
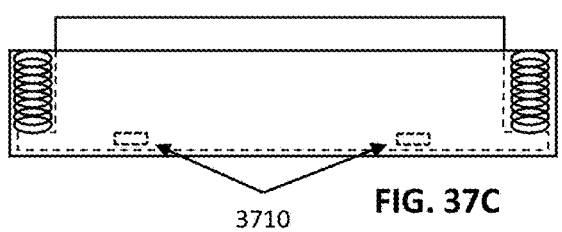

FIG. 37C discloses a long side view of a magnetic compartment in a latched configuration according to an embodiment of the invention.

Figure 37D:
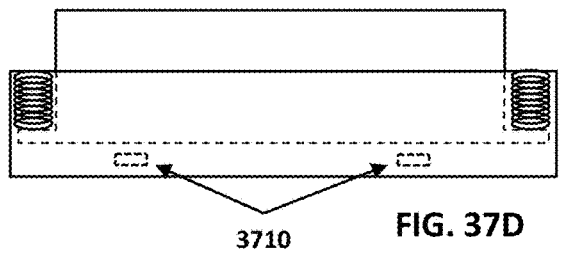

FIG. 37D discloses a long side view of a magnetic compartment in a released configuration according to an embodiment of the invention.

Figure 38:
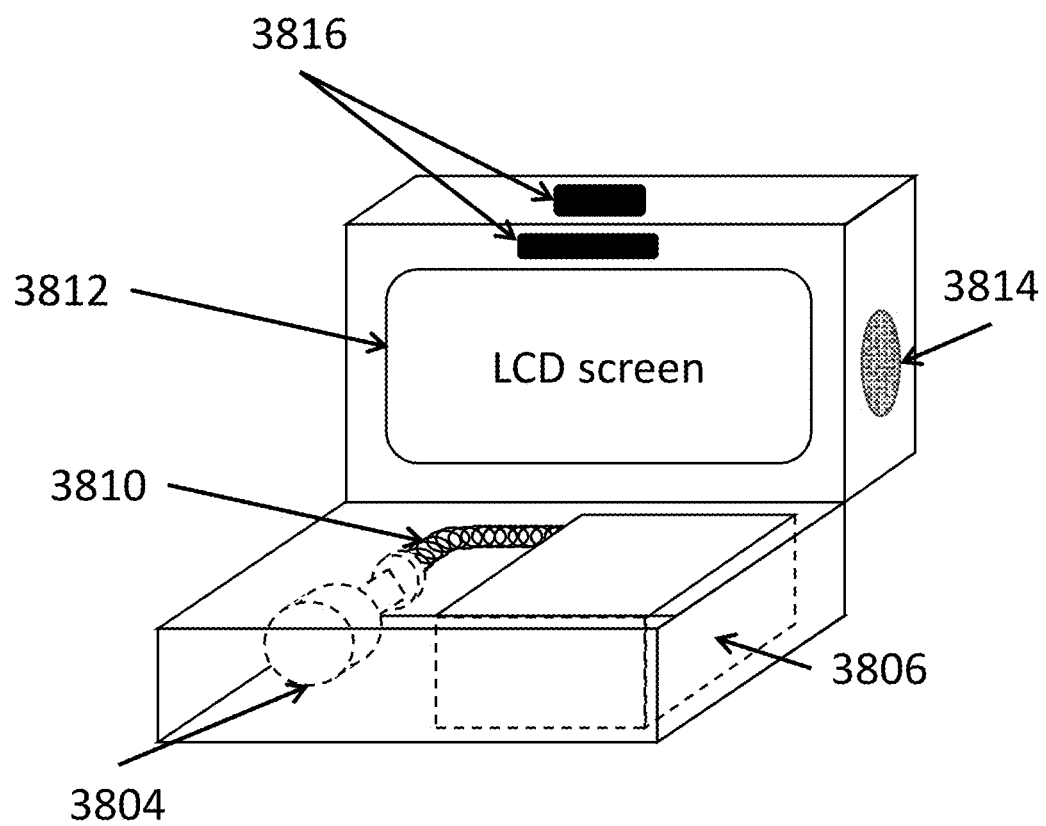

FIG. 38 discloses a magnet case that is designed to carry and operate a handheld external magnet

DETAILED DESCRIPTION

The present invention discloses intragastric medical devices which may be implanted within a patient's body without surgery, and controlled remotely with external devices using the forces of magnetic attraction and repulsion. Deployable devices that may be inserted into the stomach of a patient include devices containing flexible or rigid magnetic materials in a variety of shapes, sizes, and orientations. Devices whose structure is formed from a flexible and resilient material deploy immediately when they are no longer restrained. Although deployable devices can be restrained in many ways, this is often effectuated by the patient's esophagus, an overtube, or sutures binding the device in the collapsed position during transesophageal insertion or removal, which are endoscopically removed from the device inside the stomach. Fluid-filled devices are deployed by filling their bladders with fluid.

The orientation and position of such devices, e.g., a collapsible frustacone-shaped device, or a lantern shaped device, may be adjusted remotely with an external device containing magnetic material. The magnetic materials of the internal and external devices may include any magnets, magnetizable materials, and ferrous metals apparent to persons of ordinary skill in the art such as iron, nickel-iron, silicon-iron, cobalt-iron, neodymium, magnetic powder, amorphous and nanocrystalline alloys, ferrite powder, rubber polymer resins, mixtures and alloys of the foregoing, and for external devices, electromagnets. Such magnetic materials may be positioned on the interior or exterior surface of a device, or may be integral thereto.

The disclosed systems, combinations of magnetic materials capable of attracting one another, devices, and methods are susceptible to implementation in various embodiments and the disclosure of specific embodiments is not intended to limit the scope of the invention as claimed unless expressly specified. The invention will now be described in connection with certain embodiments and drawings so that it may be more fully understood. With specific reference to the embodiments and figures in detail, it is stressed that the particulars presented are by way of example for purposes of illustrative discussion of embodiments of the present invention only and are presented to provide what is believed to be the most readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1A:
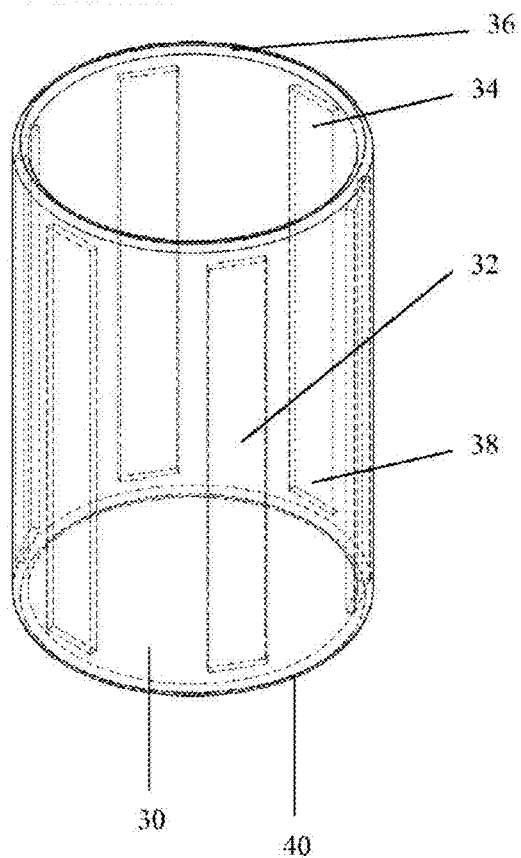
FIG. 1A is a perspective view of a collapsible tubular intragastric device.
Figure 1B:
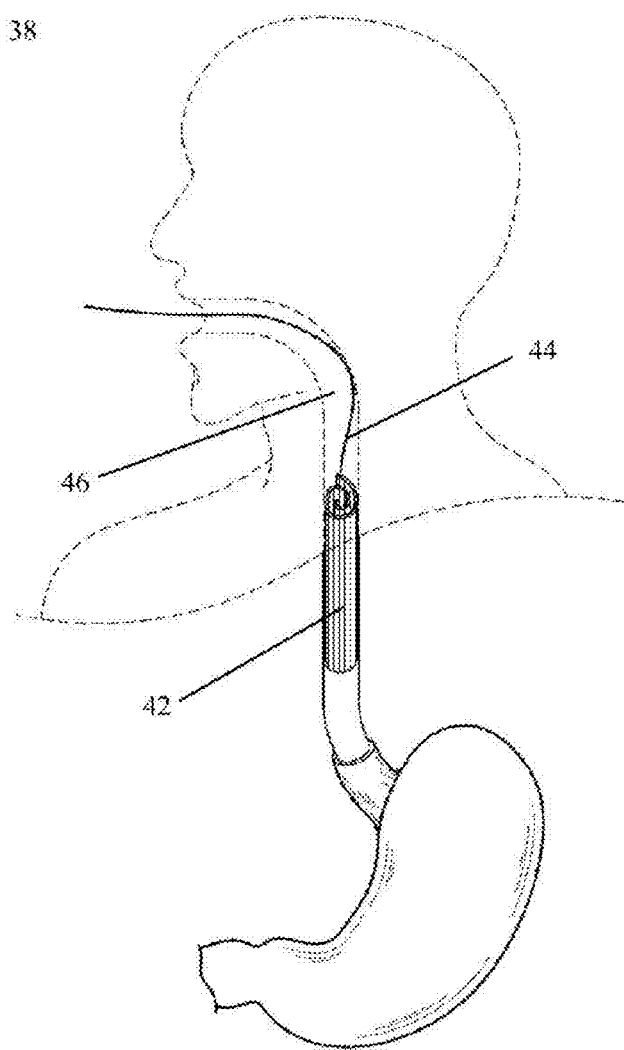
FIG. 1B is a perspective view of the esophageal insertion of a collapsed intragastric device.

A first embodiment of an intragastric device is presented in FIG. 1A, which shows a perspective view of a tubular intragastric device in its default deployed state, during which its flexible and resilient tubular structure (30) forms a hollow cylindrical passage, around which 6 sealed compartments capable of containing magnetic materials are circumferentially distributed within the tubular structure's flexible and resilient material, containing 6 bar magnets (32) with their north poles (34) facing the top of the device (36) and south poles (38) facing the bottom of the device (40). FIG. 1B shows the device of FIG. 1A in the collapsed state (42) reversibly attached to an endoscope (44) that is pushing the device through the patient's esophagus (46). Once such a resilient collapsible device exits the esophagus, the device's resilient and flexible structure reverts to its natural deployed
state, as shown in FIG. 1A. While endoscopic insertion is disclosed in FIG. 1A, several other methods of insertion will be apparent to the persons of ordinary skill in the art, as will the use of fluoroscopic guidance when advantageous. Without limitation, alternative insertion methods may include the placement of an endoscope in the stomach, passing a guidewire into the stomach through the endoscope's working channel, redrawing the endoscope, and passing an intragastric device over the guidewire with a delivery caster. Similarly, practitioners may load an overtube onto an endoscope used to place the overtube from the mouth to the distal esophagus or stomach before redrawing the endoscope and passing the intragastric device through the overtube's lumen, which may also accommodate any other instruments used to support the intragastric device.

Figure 2A:
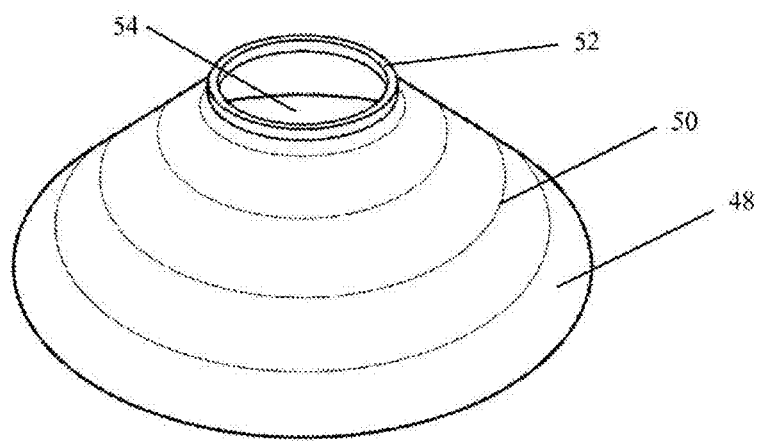
FIG. 2A is a perspective view of a ring magnet embodiment of the collapsible intragastric device.
Figure 2B:
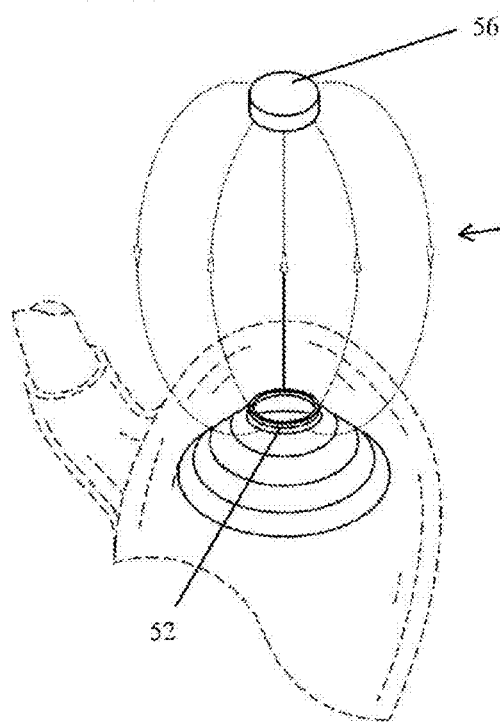
FIG. 2B is a perspective view of a ring magnet embodiment of the collapsible intragastric device being subjected to slight magnetic force with an external magnet.
Figure 2C:
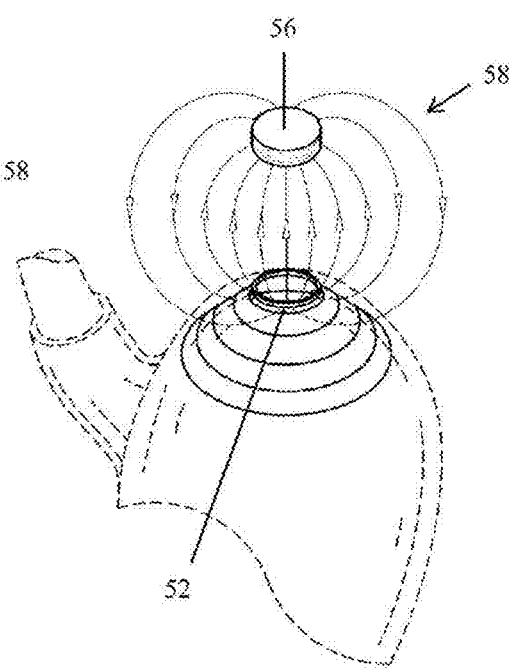
FIG. 2C is a perspective view of the intragastric device in a patient's stomach being subjected to moderate magnetic force with an external magnet.

Referring now to FIG. 2A, the collapsible intragastric device comprises a frustacone-shaped structure (48) which is primarily constructed from a resilient and flexible material with textured ridges (50) encircling a ring magnet (52) small enough in diameter to slide down a patient's esophagus and containing a hollow central passage (54). FIG. 2B shows the collapsible intragastric device in a patient's stomach with an external magnet (56) positioned outside the patient's body just close enough to the intragastric device to create a slight attractive force between the intragastric device's ring magnet (52) and external magnet (56), as represented by the magnetic field lines (58) running from the external magnet's north pole to the ring magnet's south pole and from the ring magnet's north pole to the external magnet's south pole. FIG. 2C shows the external magnet (56) positioned outside the patient's body and close enough to the intragastric device to create a strong attractive force between the ring magnet (52) and the external magnet (56) represented by a larger number of magnetic field lines (58) between the devices.

Figure 3A:
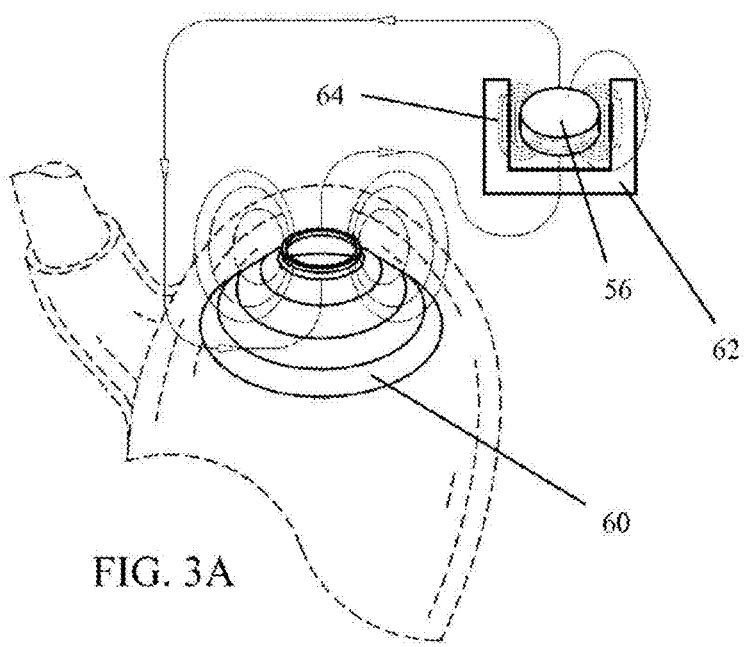
FIG. 3A is a perspective view of an external shell of high magnetic permeability diverting most of an external magnet's field lines away from an intragastric device.
Figure 3B:
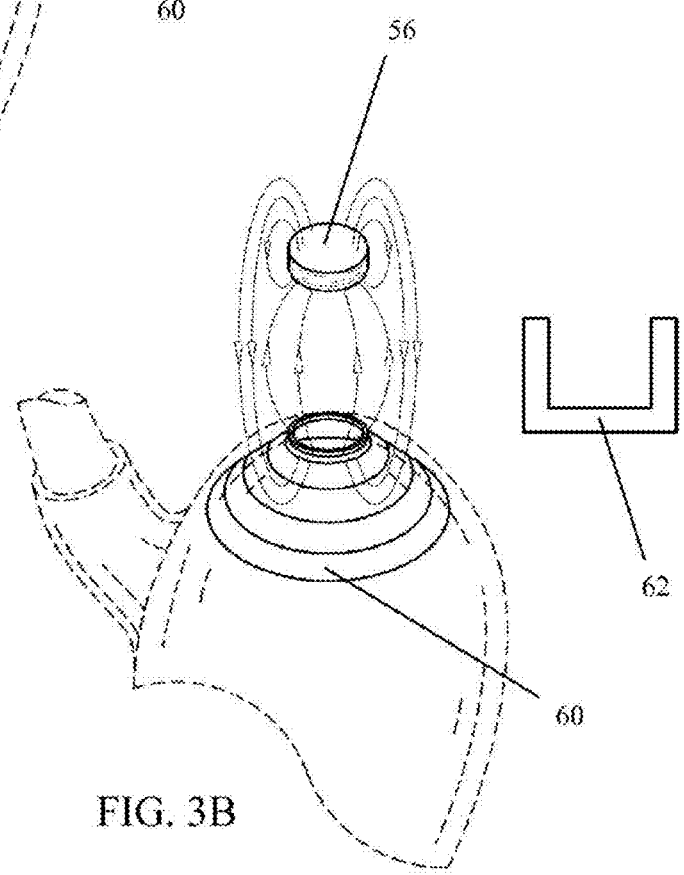
FIG. 3B is a perspective view of an external magnet attracting an intragastric device after removal from a shell of high magnetic permeability.

Another embodiment of the satiety-inducing system's external components seeks to address the need for safety and convenience of adjustability. For example, the more than 50-fold increase in magnetic field strength that can occur as the separation distance between magnets is reduced from 13 inches to 2 inches comes with acknowledged risks of discomfort, injury, and attractive forces great enough to impair patients' ability to move external magnets away from their torso. In addition to maintaining a safe distance between magnetic materials, magnetic field lines can be diverted away from the stomach with a moveable shell, case, or sleeve of high magnetic permeability that can be slid into place to reduce attractive force. FIG. 3A shows a an external magnet (56) close enough to an intragastric device (60) to create a strong attractive force, which is nonetheless producing only a nominal pulling force due to the positioning of the external magnet within a shell of high magnetic permeability (62), which has diverted the majority of the external magnet's field lines (64) away from the intragastric device (60). FIG. 3B shows a strong attractive force occurring between the intragastric device (60) and external magnet (56) of FIG. 3A, as applied to the stomach wall by the intragastric device, due to the removal of the external magnet (56) from the shell of high magnetic permeability (62) despite maintaining a distance between the intragastric and external devices similar to that in FIG. 3A. Finally, when a permanent reduction in the strength of the magnetic field emanating from the external device in a particular direction is desired, such as to prevent interference with other electronic devices, a shell, case, sleeve, or coating of high magnetic permeability may be affixed to a smaller portion of the external device to provide these benefits without necessitating the removal depicted by FIGS. 3A-B in order to attract an intragastric device.

Figure 4A:
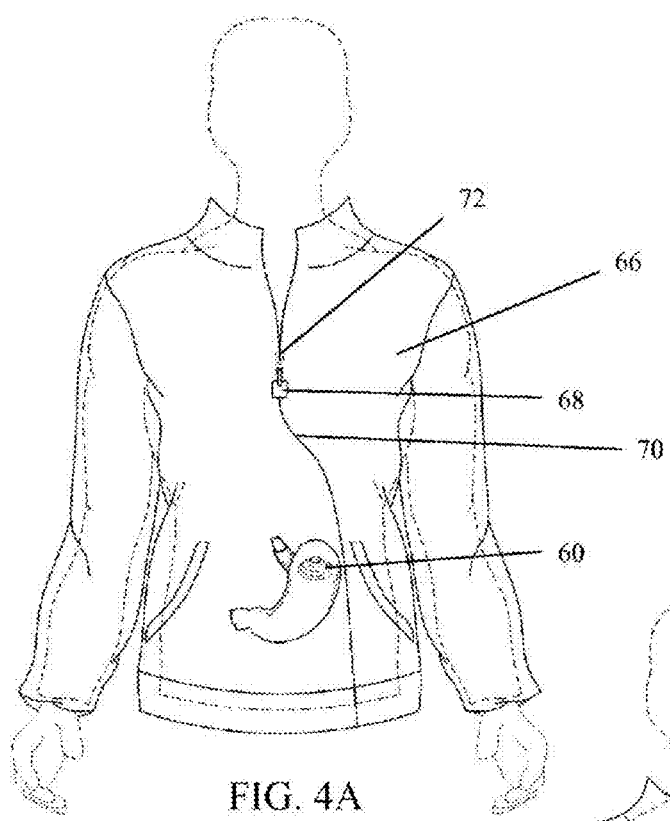
FIG. 4A is a perspective view of a piece of magnetic apparel in the unactivated position.
Figure 4B:
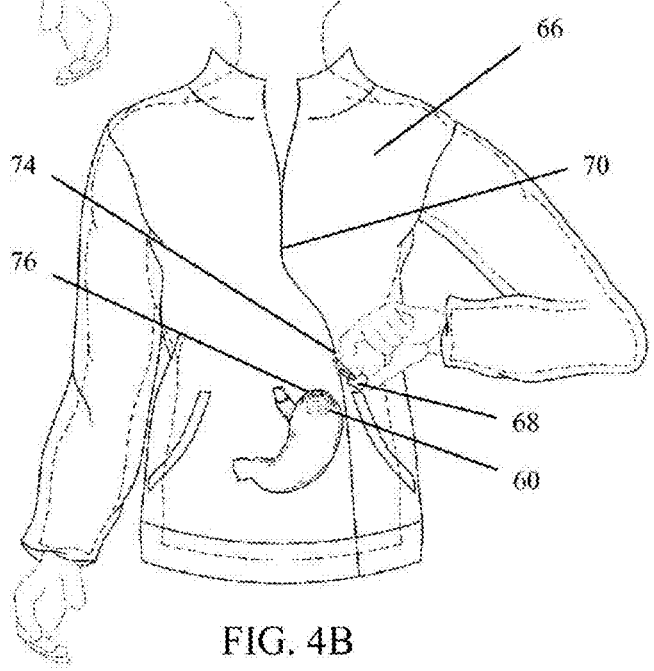
FIG. 4B is a perspective view of a piece of magnetic apparel in the activated position.

Yet another embodiment of the satiety-inducing system addresses the need for predictable positioning of the external magnet, as well as practical means for carrying it around throughout the day. FIG. 4A shows a piece of apparel (66) with an external magnet (68) attached to a zipper (70) in the upper position (72), which is a large enough distance from the intragastric device (60) to create only a nominal pulling force. FIG. 4B shows a piece of apparel (66) with an external magnet (68) attached to a zipper in the lower position (74), which is close enough to the intragastric device (60) to create a strong pulling force between the external magnet and intragastric device, which is applied in the form of tactile stimulation to the inner stomach wall (76) to induce the feeling of satiety. Finally, components of high magnetic permeability such as those depicted in FIGS. 3A-B and methods of preventing undesired magnet and zipper travel apparent to persons of ordinary skill in the art such as pockets, buttons, and hook-and-loop fasteners may be integrated into the apparel. While compounds of high magnetic permeability may be integrated into any part of the apparel, an exemplary application can occur at the upper position (72) for a number of reasons, including diversion of magnetic field lines away from the intragastric device to further reduce the pulling force, reduction of the travel distance between the upper and lower positions, and prevention of magnetic interference with, or attraction to, other magnetically sensitive objects.

Figure 5A:
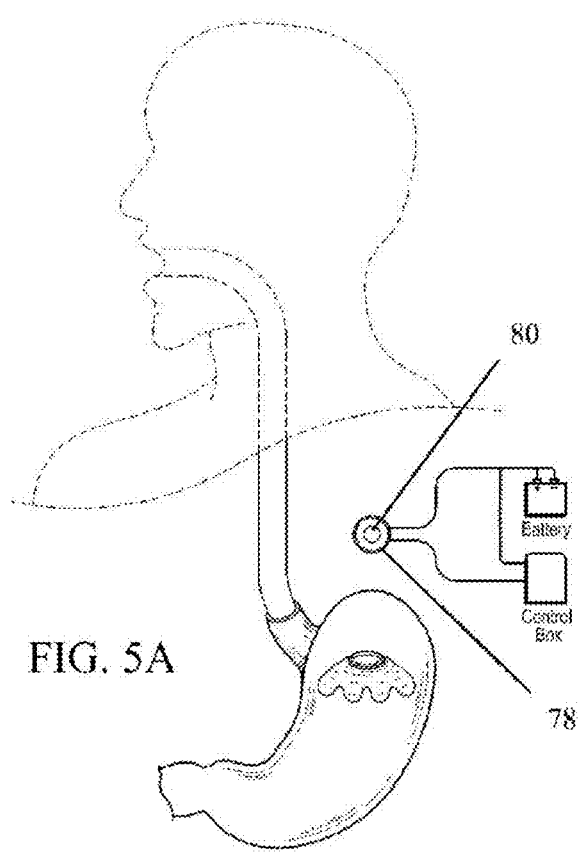
FIGS. 5A-B are perspective views of an external electromagnet system.
Figure 5B:
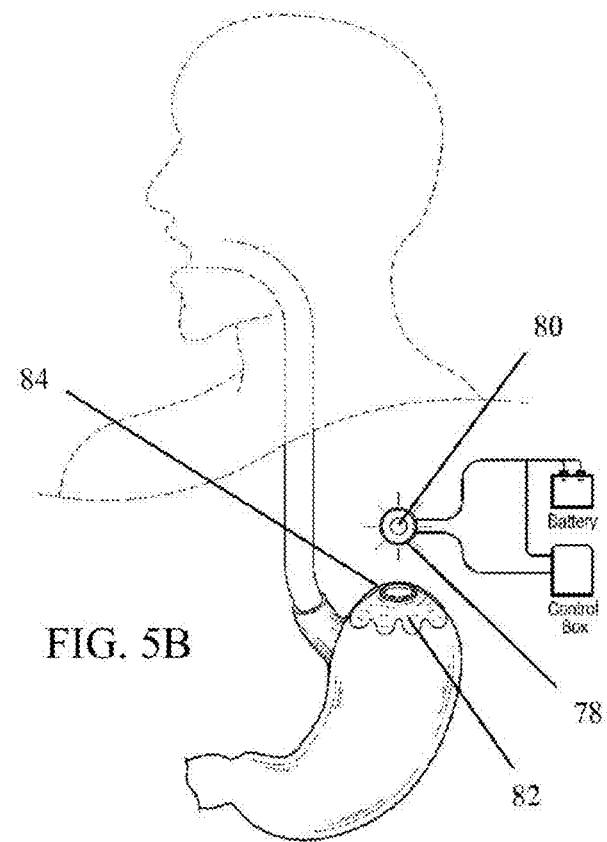

When an alternative to conventional magnetic material in the external portion of the satiety-inducing system is desired, electromagnets may also be used. FIG. 5A shows an external electromagnet system which comprises an electromagnet (78) with ferromagnetic core (80) and a control box containing an electron throttle that is completely barring the flow of electrons from the battery into the electromagnet. FIG. 5B shows the external electromagnet of FIG. 5A with an electric current flowing from the battery into the electromagnet to create a strong enough magnetic field to attract the collapsible frustacone-shaped intragastric device (82) towards, and impart stimulating force upon, the inner stomach wall (84), to induce the feeling of satiety.

For applications where buoyancy, volumetric distention, or other attributes of inflatable devices are deemed advantageous, inflatable bladders may be used. FIG. 6A shows an intragastric device in the deflated state for transesophageal insertion and removal with an endoscope (86) that pumps fluid into or out of the bladder (88) formed by the device's flexible skin (90) through a sealing valve (92) to facilitate intragastric device deployment, and may optionally include a snare loop to streamline transesophageal retrieval. The skin also includes embedded magnets (94) which optionally protrude from the flexible skin to augment the tactile stimulation imparted upon the inner stomach wall by the device. FIG. 6B shows the intragastric device of FIG. 6A in the inflated state. FIG. 6C shows the inflated intragastric device of FIG. 6B in close proximity to an external magnet (96), creating an attractive force between the devices sufficient to cause deflection (98) of the intragastric device's flexible skin as it is pulled towards, and applies stimulating force to, the inner stomach wall (100), to induce the feeling of satiety. Although FIG. 6A depicts an endoscope, it is not intended as the sole method of insertion and removal, and, along with other embodiments of the invention, several methods of intragastric device insertion and removal will be apparent to persons of ordinary skill in the art, and any appropriate methods may be used. For example and without limitation, some of the equipment that may be helpful in transesophageal insertion and removal of intragastric devices may include biopsy forceps, overtubes, guidewires, banding devices, sutures, suction cylinders, endoscopic needles, endoscopic scissors, endoscopic magnets, and endoscopic lumens through which transesophageal fluid transfer may be accomplished.

Biocompatible materials with resilient or flexible properties such as a polymer may be used in any device, such as the flexible skin (90) depicted in FIGS. 6A-C. Suitable polymers include without limitation, hydrogels, silicone, polyethylene, polypropylene, polyurethane, polycaprolactone,
polytetrafluoroethylene (PTFE), copolymers, magnetic polymers, combinations of the foregoing optionally including magnetic materials, and the like. Similarly, while biocompatible fluids such as saline solution are desirable for use in intragastric devices, acceptable fluids without limitation include air, liquids, gels, and combinations thereof. FIG. 7A shows an inflated intragastric device (102) that is inserted into the stomach and inflated by the same endoscopic process as shown in FIG. 6A. Unlike the intragastric device shown in FIG. 6A, the magnetic powder (104) contained within this intragastric device is not affixed to the skin of the device and is free to move within the confines of the bladder's inner wall. FIG. 7B shows the inflated intragastric device of FIG. 7A with an external magnet (96) in close proximity to the stomach, creating an attractive force between the magnetic powder (104) and external magnet sufficient to pull the intragastric device towards, and impart stimulating force upon, the inner stomach wall, inducing the feeling of satiety.

For this and all deployable intragastric devices, substances capable of alerting a patient or doctor that a device has failed may be embedded in the device, preferably at the most likely points of failure, such as the bladder of an inflatable device. While all substances and mechanisms of failure notification known to persons of ordinary skill in the art may be used, exemplary substances without limitation may include methylene blue as well as dyes capable of altering a patient's stool or urine in a manner sufficient to provide notice of latent device failure, or providing intragastric coloration that can be observed through an endoscope to aid in the process of ascertaining the location, type, and severity of device abnormalities.

Figure 8:
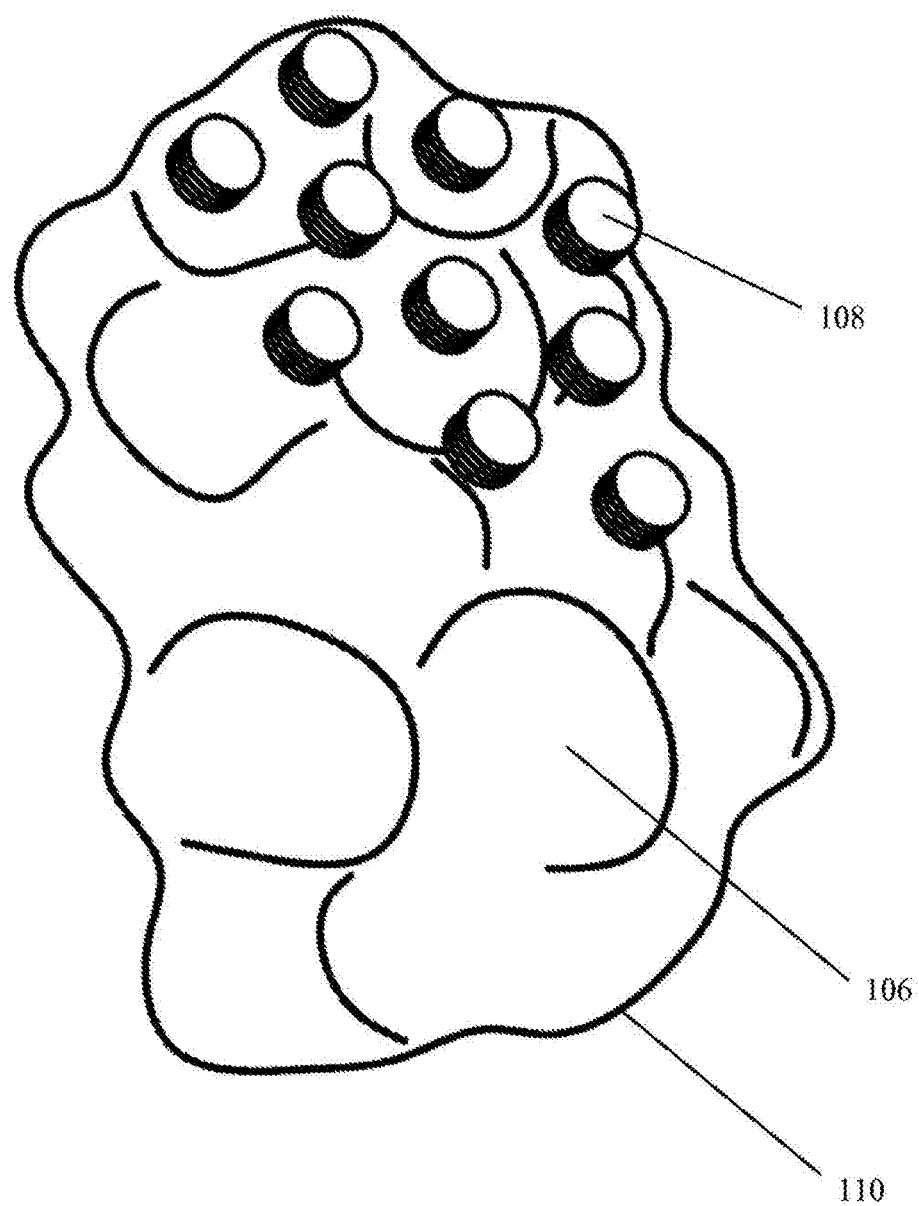
FIG. 8 is a perspective view of an inflated intragastric device with rounded protrusions.

FIG. 8 shows an alternative embodiment of an inflatable intragastric device constructed primarily from a flexible and resilient skin which constitutes a fluid bladder that can either be endoscopically filled and drained within the stomach in the manner shown in FIGS. 6A-C, or manufactured in a size small enough to stretch into a substantially cylindrical shape to slide through the esophagus in the filled state. The device contains variably sized rounded protrusions (106) and hemispherically localized magnets (108) integrated into the device's flexible skin (110), which protrude from the device to impart tactile stimulation upon the stomach wall and induce the feeling of satiety.

Figure 9:
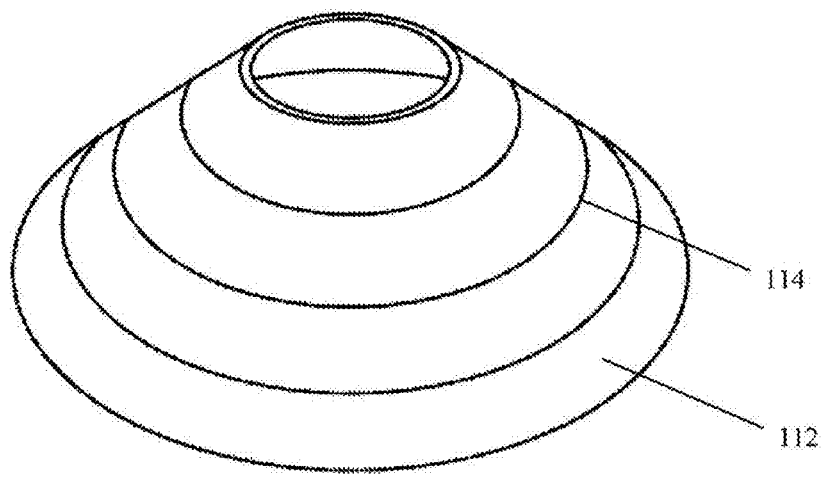
FIG. 9 is a perspective view of a collapsible frustacone-shaped intragastric device.

When a more uniform distribution of magnetic material throughout the device is desired, or simplifies the manufacturing process, fine magnetic materials such as magnetic powder may be integrated in the flexible and resilient material that forms the primary structure of the device. As is the case with all embodiments, in the event that this process forms a material that is not biocompatible, the device may be coated with a biocompatible material. FIG. 9 shows a collapsible frustacone-shaped intragastric device constructed entirely from a flexible and resilient magnetic compound (112) with textured ridges (114) which can be collapsed for transesophageal insertion into, and removal from, the stomach. As is the case with all other devices, magnetic materials may be added to an endoscope to help facilitate the transesophageal insertion and retrieval of intragastric devices.

Figure 10A:
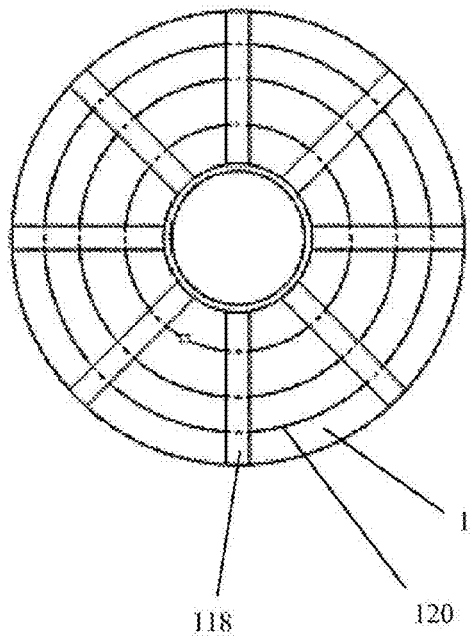
FIG. 10A is a top plan view of a collapsible frustacone-shaped intragastric device with integrated bar magnets.
Figure 10B:
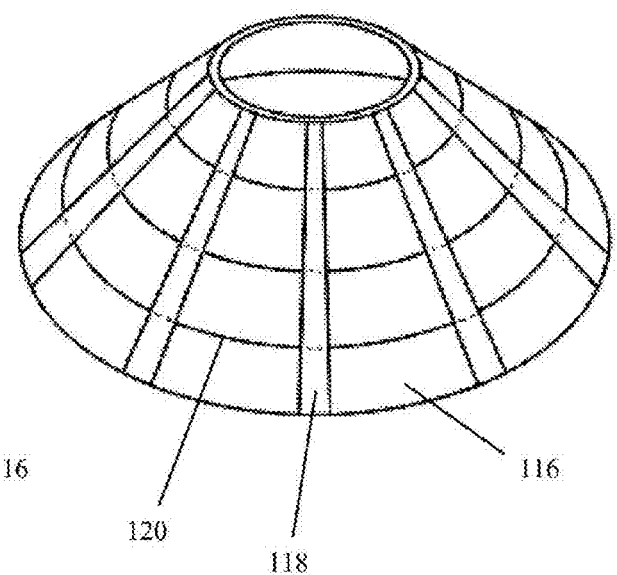
FIG. 10B is a perspective view of a collapsible frustacone-shaped intragastric device with integrated bar magnets.

FIG. 10A shows a collapsible intragastric device which comprises a flexible and resilient frustacone-shaped structure (116) with 8 circumferentially distributed bar magnets (118) embedded in the frustacone-shaped structure with three suture loops (120) traveling through the upper, mid, and lower portion of each bar magnet, securing them both to one another and the frustacone-shaped structure within which they are embedded. FIG. 10B is a top plan view of the intragastric device of FIG. 10A.

Figure 11A:
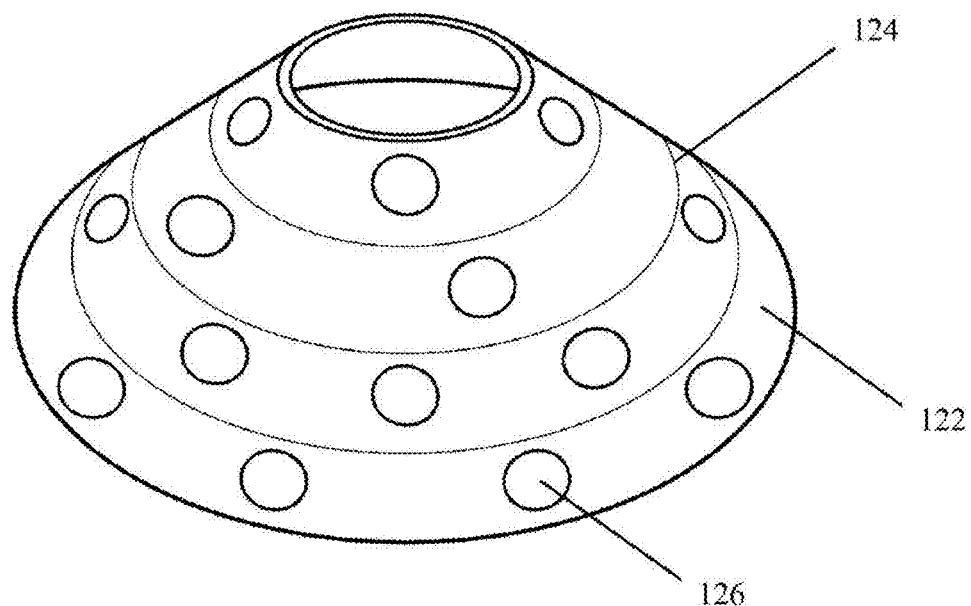
FIG. 11A is a perspective view of a collapsible frustacone-shaped intragastric device with integrated disc magnets.
Figure 11B:
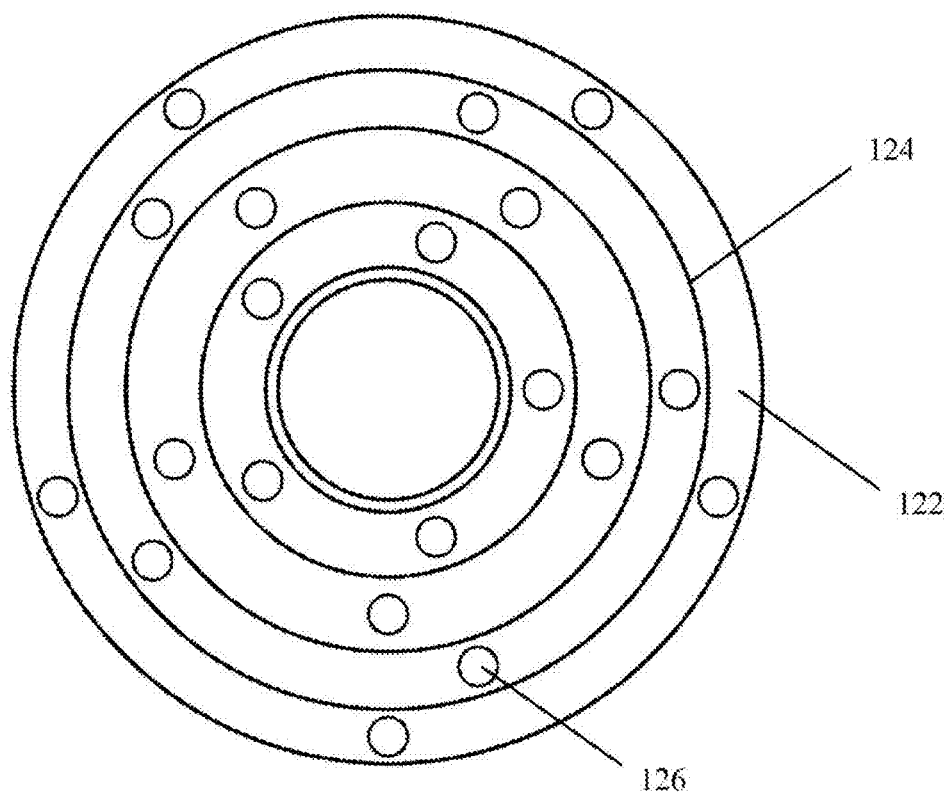
FIG. 11B is a top plan view of a collapsible frustacone-shaped intragastric device with integrated disc magnets.

FIG. 11A shows a collapsible intragastric device which comprises a flexible and resilient frustacone-shaped structure (122) with raised textured ridges (124) and embedded disc magnets (126) circumferentially distributed inside of the biocompatible frustacone-shaped structure. FIG. 11B is a top plan view of the intragastric device of FIG. 11A.

Figure 12:
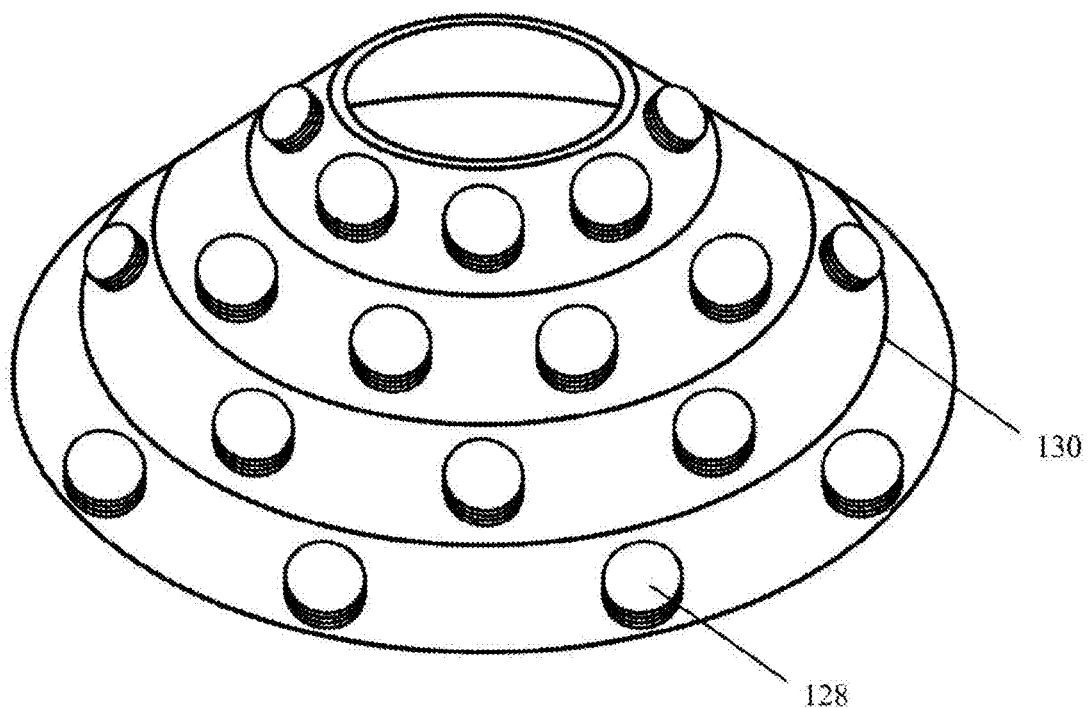
FIG. 12 is a perspective view of a device comprising the flexible and resilient frustacone-shaped structure of FIG.

FIG. 12 shows an intragastric device comprising the flexible and resilient frustacone-shaped structure of FIG. 11A, outfitted with protruding cylindrical magnets (128), embedded resilient loops (130), and a biocompatible coating capable of stimulating the inner wall of a patient's stomach to induce the feeling of satiety.

FIG. 13 shows a collapsible intragastric device which comprises a flexible and resilient structure in a frustacone shape (132) with embedded resilient loops (134) and swiveling magnets with a biocompatible coating (136) protruding from the outer surface of the structure to impart tactile stimulation upon the inner wall of a patient's stomach and induce the feeling of satiety.

When an even greater degree of change to magnetic materials' orientation relative to the device within which they are installed is desired, magnetic materials may be confined within a designated section of a device without further restricting their movement. Allowing magnets to shift in this manner can ensure external devices' ability to magnetically attract intragastric devices regardless of their orientation. In other words, this manner of construction allows a magnetic device's polarity to change even when the orientation of the device cannot change.

FIG. 14A is a perspective view of a collapsible intragastric device comprising a flexible and resilient frustacone-shaped structure (138) that envelopes 6 sealed compartments (142) capable of securing magnetic materials, which are partially filled with unrestrained magnetic powder (140)

which is not being subjected to any external magnetic fields. The intragastric device also contains a hollow central core (144) through which stomach contents may pass and within which an endoscope may be attached for transesophageal insertion and retrieval. FIG. 14B is a bottom plan view of the intragastric device depicted in FIG. 14A. FIG. 14C is a side elevation view of the intragastric device depicted in FIG. 14A. While depicted in an intragastric embodiment, this method of construction is equally applicable to external magnetic devices.

FIG. 15A is a perspective view of the collapsible intragastric device of FIGS. 14A-C with its unrestrained magnetic powder (140) in the upper portion of the 6 sealed compartments (142) due to the presence of an external magnetic device (148) positioned close enough to the intragastric device to create an attractive force between the magnetic powder and the external magnetic device sufficient to pull the intragastric device towards, and impart stimulating force upon, the inner wall of the patient's stomach to induce the feeling of satiety in the same manner depicted in, e.g., FIGS. 7A-B. FIG. 15B is a bottom plan view of the intragastric device depicted in FIG. 15A. FIG. 15C is a side elevation view of the intragastric device depicted in FIG. 15A.

Where increased rigidity or structural integrity is desired, e.g., during endoscopic insertion and retrieval, resilient mesh may be integrated in or attached to any intragastric device. Similarly, resilient mesh may also be attached to magnetic materials within the device to provide an extra degree of protection against separation of magnetic materials within the gastric lumen in the event that the structural integrity of a device becomes compromised. Finally, a suture loop may be threaded through resilient mesh to facilitate endoscopic collapse and removal of the device. FIG. 16A is a perspective view of resilient mesh (150) capable of being embedded in the structure of any intragastric device, and shown embedded in the collapsible tubular structure (152) of the intragastric device depicted in FIGS. 1A-B. A single suture loop (154) is also depicted, threaded through the upper portion of the mesh, which can be pulled away from the device to streamline transesophageal removal by reducing the circumference of the upper portion of the device and causing it to collapse inwards and push any stomach contents that may be residing in the device's hollow core out through the bottom of the device. While many additional methods of inserting and removing this intragastric device will be apparent to persons of ordinary skill in the art, tools appropriate for orienting the device within the gastric lumen and pulling the depicted suture loop may include without limitation biopsy forceps, suction cylinders, and endoscopic magnets. Other equipment and methods of streamlining suture recovery may be used as well, such as incorporating snare loops into the suture loop, and using a suture whose color is distinguished from the remainder of the device, FIG. 16B is a side elevation view of the resilient mesh (150) and intragastric device of FIG. 16A. FIG. 16C is a bottom plan view of the resilient mesh (150) and intragastric device of FIG. 16A.

FIG. 17A is a perspective view of a collapsible cone-shaped intragastric device comprising a flexible and resilient frustacone-shaped structure (156) which encircles a cylindrical piece of magnetic material (158) with a chamfered edge (160) and narrow central channel (162), into which instruments may be inserted to securely grasp the device and dictate its orientation. In contrast to FIGS. 2A-C, this device's narrow central channel (162) is formed with additional magnetic material which envelops the hollow central channel, which also increases the amount of magnetic material in the device, and derivatively, the amount of pulling force that can be created in communication with an external magnetic device. When a reduction in the intragastric device's pulling force, weight, or collapsed size is desired, the outer diameter of the cylindrical magnetic material and inner diameter of the frustacone-shaped structure may be reduced by the same amount. Like many other embodiments, an external magnetic device may be used to attract the device of FIGS. 17A-C towards, and impart stimulating force upon, the inner wall of a patient's stomach to induce the feeling of satiety. FIG. 17B is a top plan view of the intragastric device of FIG. 17A. FIG. 17C is a side elevation view of the intragastric device of FIG. 17A.

Yet another embodiment of the satiety-inducing system addresses the need for predictable positioning of the external magnet, as well as practical means for carrying it around throughout the day. FIG. 18A is a perspective view of a belt containing an external magnetic device in the lower position. FIG. 18A shows a piece of apparel (166) such as a shirt being worn by a patient. A belt (167) is strapped across the waste of the patient. Attached to belt (167) is a magnet container device (170) which contains an external magnet (168) attached to a handle (169). The patient uses the handle to move the external magnet (168) from a lower position to a higher position and vice versa. In alternative embodiments, the external magnet surface is covered with a coating (such as plastic or teflon), and the handle and the plastic casing could be one unit. That is, FIG. 18A shows the external magnet (168) in the lower position, with intragastric device (172) in the bottom portion of the patient's stomach. A patient has the ability to move the intragastric device (172) towards the stomach wall by putting on the belt with the external magnetic device in the lower position, capturing the floating intragastric device in a lower position and then moving the external magnet (168) to an upper position, such as in FIG. 18B, such that the intragastric device is pressed against the stomach wall to induce a feeling of satiety.

FIG. 18B is a perspective view of a belt containing an external magnetic device in the upper position. FIG. 18B shows a piece of apparel (180) such as a shirt being worn by a patient.

A belt (181) is strapped across the waist of the patient. Attached to the belt (181) is a magnet container device (182) which contains an external magnet (184) attached to a handle (183) in an upper position, which is close enough to the intragastric device (185) to create a strong pulling force between the external magnet (184) and intragastric device (185) such that the intagastric device is pressed against the stomach wall of the patient. The patient can use handle to move the external magnet (168) back from the higher position to a lower position.

Ghrelin or the "hunger hormone", also known as lenomorelin (INN), is a peptide hormone produced by ghrelinergic cells in the gastrointestinal tract. When the stomach is empty, ghrelin is secreted. When the stomach is stretched, secretion stops. It can be appreciated that moving an external magnet from a lower position such as that shown in FIG. 18A to an upper position such as that shown in FIG. 18B would stimulate and expand the inner stomach wall and thus stop secretion of the hormone ghrelin, thus adding to the feeling of satiety of the patient.

FIG. 19A illustrates an embodiment of a magnet container device (202). In the depicted figure, a magnet container device (202) is attached to a belt (201) which is intended to be strapped across the waste of a patient. External magnet (203) comprises a permanent magnet source which is intended to attract an intragastric device. Attached to external magnet (203) is a handle (204) which is used by a patient to move the external magnet from a lower position to an upper position, thus moving an intragastric device comprised of magnetic material to an upper position within the stomach.

The embodiment shown in FIG. 19A addresses the situation where it may be desirable to immediately cut off the magnetic force of the external magnet. To accomplish this, magnet container device (201) contains a shield chamber (205) where a patient can slide in a shield which interferes with the magnetic field. In alternative embodiments, a shield can be deployed after external magnet is in an upper position for a predetermined amount of time. For example, a timer could be triggered when the external magnet is moved into an upper position and reset when the external magnet is moved back into a lower position. The shield could be automatically deployed via a simple sliding mechanism when the timer reaches 30 minutes. This timer could be utilized as a safety measure in case the patient forgets to move the magnet back into a lower position, so that the intagastric device does not remain pushed against the stomach wall of the patient.

In some embodiments, the magnet container device has additional features where the simplicity of the design of magnet container device 201 is not desired. The magnet container device (211) depicted in FIG. 19B displays an example of such an embodiment. FIG. 19B is an embodiment of a magnet containing device where a second external magnet (215) is utilized to create additional force. It can be appreciated that two identical magnets stacked directly on top of each other behave similar to a solid magnet of the same dimensions as the two stacked magnets. Thus, magnet container device (211) advantageously provides added flexibility in adding and removing additional magnetic force by utilizing a second magnet to create additional force. For example, a patient may require more force to grab the intragastric device at a lower position, so both magnets could be utilized at the lower position and moved to a top position. When the patient wants to create additional force, the patient can move the second external magnet (215) towards the upper position via a second handle (216). That is, when an addition of the pulling force in the upper position is desired, the embodiment illustrated as magnet container device 301 advantageously provides a second external magnet. Alternatively, when the patient wants to create additional force at a lower position to grab the intragastric device, the patient can have both external magnets (215) in the lower position and move them both to the upper position. Once the intagastric device has been captured and moved to the upper position, the second external magnet can be moved back to reduce the force at the upper position.

Magnet container device (201) also contains an upper shield chamber (217) for interfering between the two external magnets, as well as a lower shield chamber (214) where a patient can cut off the magnetic attraction with the intragastic device.

The present disclosure provides for multiple embodiments for a patient positioning an external magnetic device by moving the external magnetic device from a lower position to a upper position. FIG. 20A illustrates an embodiment of a magnet container device (302) which provides for moving an external magnetic device. Magnet container device (302) contains an external magnet (303) attached to a handle (304). The external magnet has wheels (305) which run on tracks (306) which are mounted on the bottom of magnet container device (302). A patient moves the external magnet via handle (304) from a lower position to an upper position, and vice versa.

FIG. 20B illustrates a track mechanism for moving an external magnet (309) where the magnet (309) has wheels (310) that runs on a track (308) which is directly attached to belt (307). It can be appreciated that this embodiment does not utilize a magnet container device, and a patient simply grabs the external magnet directly to moves it along the track from a lower position to an upper position, and vice versa.

FIG. 20C illustrates a rail mechanism for moving an external magnet whereby the external magnet (313) contains a hole (314), and a rail (313) attached to a patient's belt (311) is run through a hole (314). It can be appreciated that this embodiment does not utilize a magnet container device or a track, and a patient simply grabs the external magnet directly to moves it along the rail (313) from a lower position to an upper position, and vice versa.

In some embodiments, the mechanism for moving the external magnet does not include wheels, rails, or tracks. For example, in one embodiment the inner walls of the magnetic container device are covered with a smooth material such as felt to reduce friction with the magnet, such that the external magnet can be moved smoothly by a patient using handle without the use of wheels or a track. In such embodiments, the magnet is sized to snugly fit the magnetic container device such that it can smoothly be run along the magnetic container device without utilizing any rails or tracks.

FIG. 21A illustrates a cross sectional view of an embodiment of a saucer shaped intragastric device (400). The intragastic device has a plastic exterior cover (401) and an outer wall (402) comprised of a soft material such as silicone which is designed not to scratch injure the stomach wall of the patent. An internal magnet (403) is positioned at the apex of the intragastric device (400). The intagastric device is covered by a resilient mesh (404). FIG. 21B is a top plan view of the intragastric device depicted in FIG. 21A.

FIG. 22A illustrates a cross-sectional view of a zigzag intragastric device (410) in a collapsed state for insertion into a patient's stomach via their esophagus. The intragastic device has a plastic exterior cover and an outer wall (411) comprised of a soft material such as silicone which is designed not to scratch injure the stomach wall of the patent. An internal magnet (412) is positioned at the apex of the intragastric device (400), wherein the internal magnet has a hole passing through it so that the intragastric device can be guided into the patient's stomach. Once such a resilient collapsible device exits the esophagus and enters the stomach, the device's resilient and flexible structure reverts to its natural deployed state, as shown in FIG. 22B.

FIG. 22B illustrates a cross-sectional view of a zigzag intragastric device (420) in an expanded state. An internal magnet (403) is positioned at the apex of the intragastric device (400). The bottom zig-zag edge (424) contains ridges designed with a zig-zag shape such that even if the bottom of the intragastic device is pressed against the stomach wall, digestive material such a food can still pass the ridges of the zig-zag surface. That is, the grooved surface is such that there will always be a gap between the intragastric device and the stomach wall, such that food and other materials can still pass through and around the intragastric device.

FIG. 22C is a top plan view of the zig-zag intragastric device in an expanded state depicted in FIG. 22B. It can be appreciated that ridges (430) extend from the end of the device all the way to the magnet at the apex.

FIGS. 23A and 23B show yet another embodiment of an expandable intragastric device constructed primarily from a flexible and resilient surface resembling a "lantern" shape. It can be appreciated that the lantern-shaped device is easier to move in a stomach and its smooth surface reduces the chance of irritating the inner wall of a stomach. Its spherical shape also enhances the contact area between the device and the stomach, thus better inducing satiety. FIG. 23A shows the lantern shaped intragastric device in a collapsed state prior to expansion. The expandable intragastric device contains a magnet 2302 located at the top of the intragastric device, wherein the ring magnet is small enough in diameter to slide down a patient's esophagus and contains a hollow central passage.

The collapsed state disclosed in FIG. 23A is used during delivery of the intragastric device into the stomach of the patient. Spring loaded structures 2304 expand the intagastric device upon insertion into a patient's stomach, such that mesh 2306 is expanded into a lantern shape structure. That is, once the device exits the esophagus and enters the stomach, the device's resilient and flexible structure reverts to its natural expanded state, in this case a lantern shape, via the spring loaded structures 2304 and is ready to be controlled from the outside by a patient.

FIG. 23B shows the lantern shaped intragastric device of FIG. 23A in an expanded state after endoscopic insertion. The same methods of endoscopic insertion disclosed above in the discussion of FIG. 1A may be used. Some of these methods of insertion will be apparent to the persons of ordinary skill in the art. Without limitation, insertion methods may include the placement of an endoscope in the stomach, passing a guidewire into the stomach through the endoscope's working channel, redrawing the endoscope, and passing an intragastric device over the guidewire with a delivery caster. Similarly, practitioners may load an overtube onto an endoscope used to place the overtube from the mouth to the distal esophagus or stomach before redrawing the endoscope and passing the intragastric device through the overtube's lumen, which may also accommodate any other instruments used to support the intragastric device.

In the embodiment disclosed in FIGS. 23A and 23B, the magnet 2302 is partially located outside of the lantern-shaped structure intragastric device. In an alternative embodiment, as disclosed in FIGS. 24A and 24B, the magnet is attached to but completely inside the lantern-shaped structure. In yet another embodiment, as disclosed in FIGS. 25A and 25B, the magnet is free-floating inside the lantern-shaped structure and contains self sealing plugs 2502. When the magnet is partially outside the lantern-shaped structure, it may be more easily controlled by the external magnet, while the fully imbedded attachment may provide a smoother surface and less chance of irritation and better chance of inducing satiety. Since both of these configurations have the magnet attached to the structure, the magnet will be properly aligned in removal process. In free-floating configuration, the magnet needs to be aligned first with the external magnet during removal. However, since the magnet is free to move inside the structure, it is most easily controlled by the external magnet. Self-sealing plugs 2502 are thick rubber-like material or silicon that allow wires or thin tubes to puncture through, but will seal itself after the alien object is removed.

In yet another embodiment disclosed in FIGS. 26A, 26B, and 26C, the magnet is free-floating in a balloon inside the lantern-shaped structure. FIG. 26A shows the magnet 2302 located inside a deflated balloon 2602. An airtube 2604 is used for inflating the balloon. FIG. 26B shows an inflated configuration with air tube 2604 still plugged through into balloon 2602. FIG. 26C shows an inflated configuration with the air tube removed.

FIGS. 27-32 show delivery configurations for delivery a intragastric device into the stomach of a patient, either endoscopically or non-endoscopically. One method of delivering an endoscopic device according to an embodiment comprises:
1. Going down a patient's esophagus with an endoscope, visualizing the stomach, and expanding the stomach with air;
2. Passing a guidewire through the endoscope channel into the stomach;
3. Pulling the endoscope out leaving the guidewire in place;
4. Passing an intragastric delivery device over the guidewire into the stomach via an inner catheter (also known as a stiffening tube).
5. Reintroducing scope again into the stomach to visualize the successful delivery, or xray confirming successful delivery, or measurement of catheter to confirm successful delivery.
6. Pulling a covering sheet back such that the intragastric device expands fully. In one embodiment, the device takes about 5 seconds to expand.
7. Pull back the inner catheter, which seals the self sealing plugs at the each end of the intagastric device.
8. Pull out a tip if it is suture method, or dissolving a tip. In one embodiment, the tip comprises dissolvable beads.

Figure 27:
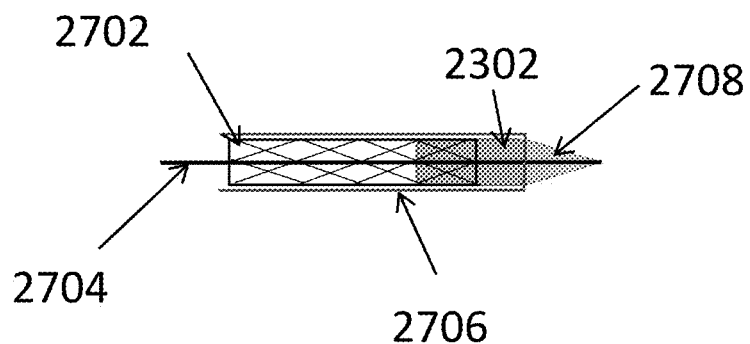
Figure 28:
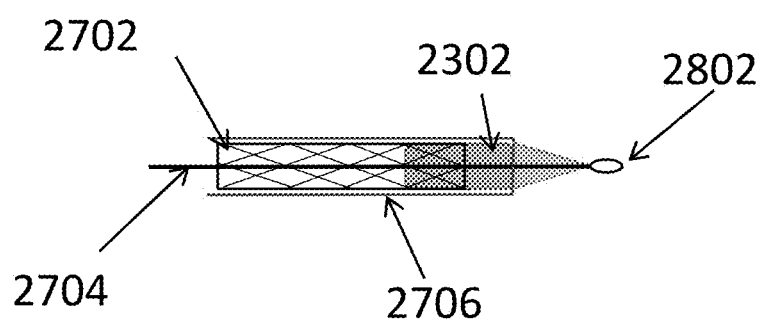

FIGS. 27 and 28 show a delivery configuration for a magnet with disk-shape stent. A magnet 2302 is placed within a meshed stent 2702. A guide wire 2704 runs though the intragastric device and is intended to guide the device through an esophagus. A dissolvable tip 2708 guides the package down a patient's esophagus and into the stomach. After insertion, a clear plastic covering sheet 2706 is removed.

FIG. 28 shows a variation where the tip is not dissolvable but is rather removed via a suture loop 2802.

Figure 29:
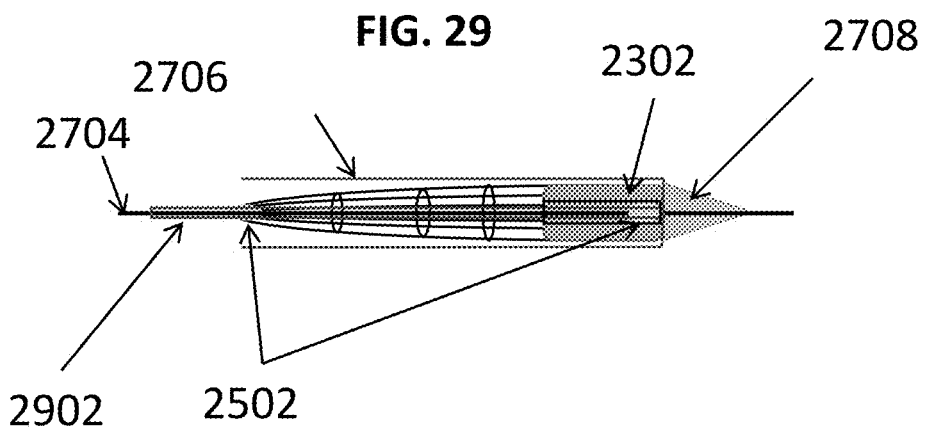

FIG. 29 shows a delivery configuration for a magnet attached to a lantern shaped stent. Magnet 2302 is attached to a mesh 2306 that expands to be a lantern shaped structure as shown in FIG. 25B. Here, a stiffening tube is used for the guide wire 2704, and air flow through the holes on the side of the tube. The stiffening tube goes through the self-sealing plugs and the magnet. The guide wire goes through the tube to reach the tip. Covering sheet 2706 holds the package together, such that when a covering sheet 2706 is pulled back the intragastric device expands fully. The stiffening tube has holes on the side, allowing air to flow into the mesh structure when it expands to a lantern shape. Self-sealing plugs 2502 seal the lantern structure after expansion.

Figure 30:
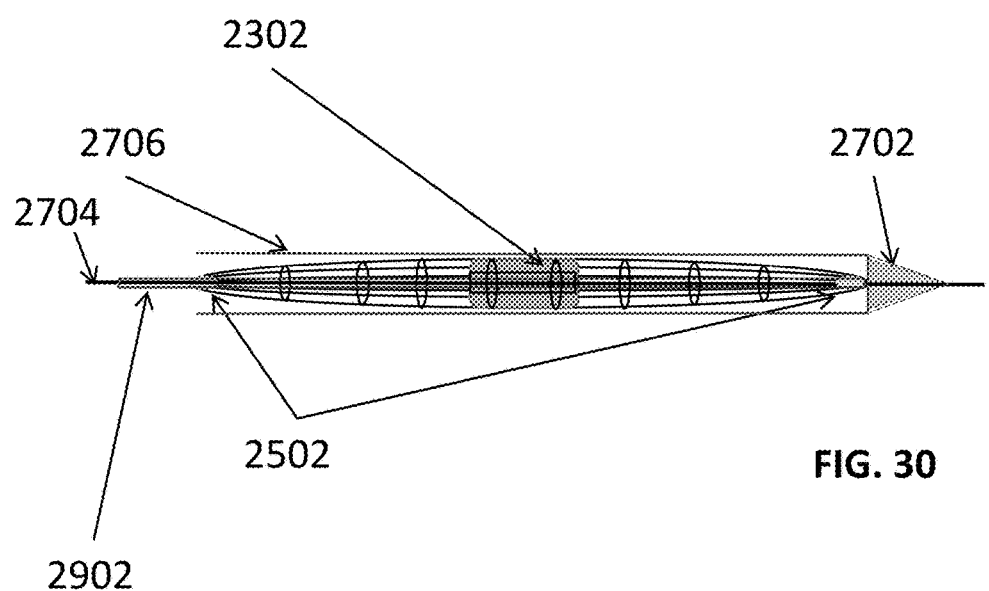

FIG. 30 shows a delivery configuration for a magnet free floating in a lantern-shape stent. Similar to FIG. 29, stiffening tube 2902 goes through the self-sealing plugs 2502 and the magnet 2302. The guide wire 2704 goes through the tube 2902 to reach the tip 2702. The tube 2902 has holes on the side, allowing air to flow into the mesh structure when it expands to a lantern shape.

Figure 31:
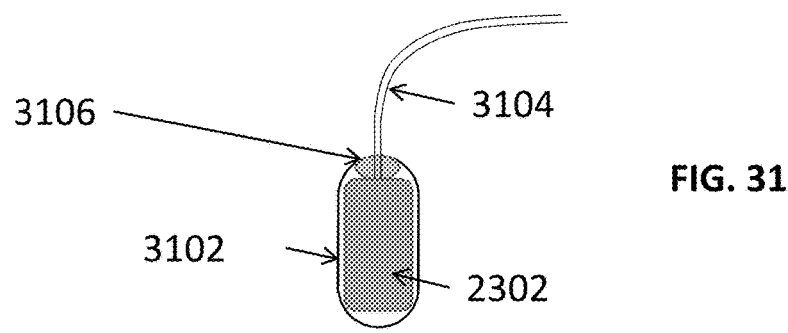

FIG. 31 shows a non-endoscopic delivery configuration via swallowing for a magnet free floating in an inflated balloon. The magnet 2302 is wrapped in a deflated balloon 3102 to be swallowed into the stomach by a patient. After the patient swallows, balloon 3102 will be inflated with the removable air tube 3104. Removable air tube 3104 is removed through self-sealing plug 3106 after the device successfully expands, wherein self-sealing plug 3106 seals the expanded balloon airtight.

Figure 32:
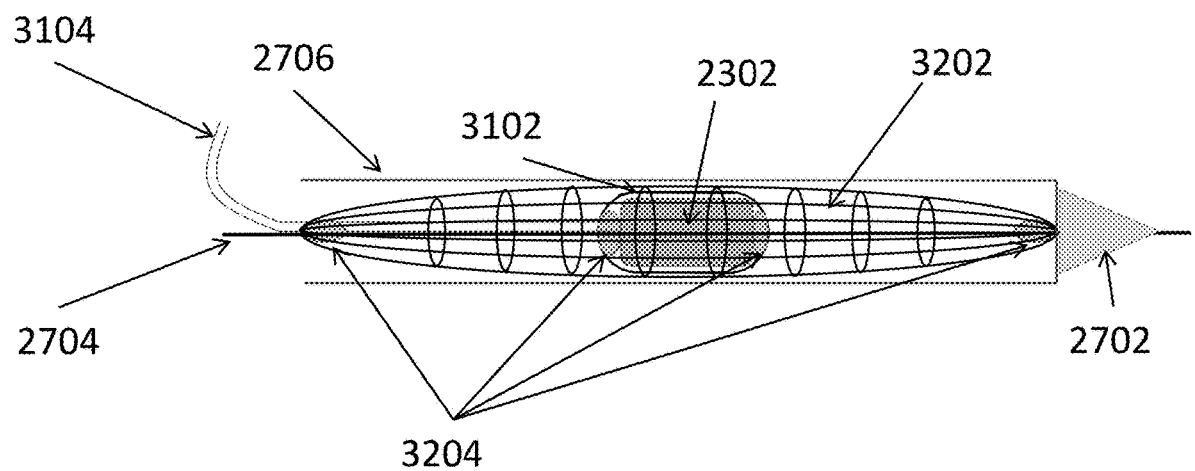

FIG. 32 shows a delivery method for a magnet free floating in an inflated balloon in a lantern structure. It can be appreciated that this embodiment discloses a combination of the previous two methods, but without a stiffening tube. The balloon is inflated via an airtube 3104 as the mesh 3202 expands, therefore there is no need for a stiffening tube. Magnet 2302 is enclosed within a balloon 3102 and the mesh 3202 that expands to be a lantern shaped structure when released.

FIG. 33 discloses an alternative embodiment where a magnet 2302 is free floating in a pre-inflated balloon 3302 in a lantern structure. The balloon 3302 is pre-inflated with sterile gas, such as $CO_2$ or $N_2$, and contains the magnet 2302 free floating within it. The balloon is enclosed by the lantern structure and compressed to fit in the covering sheet for delivery. Upon released in a stomach, the gas will decompress and inflate the balloon, allowing the device to expand to a lantern shaped structure. Self sealing plugs 2502 are located on each side of the lantern shaped structure as well as balloon 3302.

FIG. 34 discloses an alternative embodiment where a magnet is located within a pre-inflated and pre-sealed balloon of a doughnut shape with a hole through its center, allowing a guide wire to go through, thus eliminating the need of self-sealing plugs 2502 in the balloon. The magnet is free-floating in the balloon.

FIG. 35 discloses an alternative embodiment where a magnet 2302 is fixed at the center of a pre-inflated, pre-sealed balloon 3502 inside the lantern-shaped structure. The pre-inflated and pre-sealed balloon 3502 is of a doughnut shape with a hole 3502 going through its center, allowing the guide wire to go through, eliminating the need of self-sealing plugs. The magnet is not in the balloon, but fixed at the center of the hole 3502 through the balloon.

Further advances in the movement and placement of the external magnet controlled by the patient to induce satiety are presently disclosed.

FIG. 36A discloses an external view of a magnet container device according to another embodiment of the invention. The structure disclosed in FIG. 36A provides for moving an magnetic device by a patient to induce a feeling of satiety. The magnet container device contains an external magnet attached to a handle. A patient moves the external magnet the handle from a lower position to an upper position, and vice versa. In this embodiment, the magnetic container device contains latches and arms such that it can be placed in a spring loaded magnetic compartment as disclosed in FIGS. 37A-D.

FIG. 36B discloses slots located on the top slit to lock the magnet's position at a fixed position along the path from the lower position to the upper position. This may be desirable in case the patient wishes to leave the magnet in a position between the lower position and the upper position, for example when a full stretching of the stomach is not desired. In alternative mechanisms, the magnets position can be locked via handles, bolts, clips, or other well known attachment methods known in the art.

FIG. 36C discloses a side view of a magnetic container device according to an embodiment of the invention. Magnet (2414) slides along surfaces (2414) at a slope. It can be appreciated that the slope increases the distance of the magnet from the back of the magnetic compartment as it is moved from one end to the other, thus weakening the pulling force on the intragastrical device as it is pulled to an upper position. This embodiment takes advantage of the fact that a higher force may be needed to capture the intragastric magnet at the lower position than would be needed to stretch the patient's stomach at the upper position.

In one embodiment, surfaces (2414) comprise ball bearings for sliding magnet (2414) from the lower position to the upper position.

In a further embodiment providing a safety mechanism, the magnetic container device can be placed in a spring loaded compartment. The magnetic container device can be pushed in to lock into the compartment by a patient when they are ready for use, and then releases after a predetermined about of time. It can be appreciated that this provides for a safety mechanism in case a patient forgets to remove the belt or harness containing the magnetic container device, because the time release pushes out the magnetic container device to a distance away from the stomach sufficient to weaken the pulling force on the instragastric device to an amount where there is no risk of danger from the intragastic device being pushed against the stomach wall for too long.

FIG. 37A discloses a short side view of such a magnetic compartment in a latched configuration according to an embodiment of the invention. Magnet container device (2502) has been pushed inward to a locked position in the magnetic compartment. The magnetic container device is locked via latches (2510). By doing so, springs (2504) are pulled such that there is a resistance and as soon as the latches (2510) are released the magnetic container device will be pulled back up by springs (2504). The latches can be released after a predetermined amount of time by various mechanisms that would be known in the art to a person of ordinary skill. In one embodiment, a timer is set as soon as the magnetic container device is pushed in, and the latches would be released by mechanical means after the timer runs out.

FIG. 37B discloses a short side view of a magnetic compartment disclosed in FIG. 37A in a released configuration according to an embodiment of the invention. Here, the springs are in their natural pushed-in position. Once a patient wishes to use the device, the patient can push in the magnetic container device and the springs will be stretched out as disclosed in FIG. 37A.

FIG. 37C discloses a long side view of a magnetic compartment in a latched configuration according to an embodiment of the invention.

FIG. 37D discloses a long side view of a magnetic compartment in a released configuration according to an embodiment of the invention.

FIG. 38 discloses a magnet case that is designed to carry and operate a handheld external magnet 3804 for the capture and manipulation of an intragastric magnet. In an embodiment, external magnet 3804 is an electromagnet. In an The external magnet 3804 is connected to and powered by a rechargeable battery through a stretchable cord 3810. A controller unit 3806 with built-in microprocessors is integrated with the rechargeable battery to manage charging the battery and powering the external electromagnet 3804, as well as logging user information. The magnet case also includes an LCD screen 3812 to display system information and monitor patient progress, a speaker 3814 to play alarm signals and/or information for vision impaired users, and an electronic lock 3816 with a safety alarm feature.

The LCD screen 3812 and loud speaker 3814 are communicative devices to display information and sound alarm when needed. Under normal operation, the hand-held electromagnetic 3804 is removed from the case and brought close to the capture site. It is then powered by electric power to capture the intragastric magnet. Once the magnet is captured, the electric current maybe reduced to reduce magnetic force and therefore discomfort. With sufficient magnetic force, the intragastric magnet is manipulated by moving the hand-held magnet 3814 around. Each operation has a programmed time limit from when the electric current is first turned on through the electromagnet. This time limit is predetermined for safety. User can operate the magnet for shorter time but should not exceed the predetermined limit. The controller unit 3806 monitors the operation time and cuts the power when the time limit is reached. Once the power is turned off, the hand-held magnet 3804 should be returned to the case immediately and the case should be closed and locked within another programmed time from when the power is turned off. Should the magnet not be returned, or the case not be closed and locked properly within the programmed time, the LCD screen 3812 will flash and loud speaker 3814 will sound an alarm to warn the user of the proper safety procedure.

In a further embodiment, the controller unit can be programmed to oscillate an electric current in a pulsing pattern so that it alternates between a magnetic charge and no magnetic charge. It can be appreciated that this pulsing feature allows the internal device to be moved in a posterior and anterior direction within the patient's stomach. The patient can also move the handle laterally side to side while pulsing the charge, which allows the internal device to move along a three dimensional axis within the patient's stomach.

In a further embodiment, the magnet case monitors patient progress but also connects to a central platform where it is managed by a healthcare provider. For example, the magnet case can be connected through the internet to a central platform. The healthcare provider can use the data to monitor the compliance of the patient and to interact with the patient in a manner similar to telemedicine. In a further embodiment, the suitcase can be locked remotely by a healthcare provider. The device can be used both within a physician's office as well as provides for remote monitoring.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

In a further embodiment, present disclosure provides a virtual reality interface wherein a patient can see their stomach and how it is moving. The patient can also see how the intragastric device is stimulating the nerves/how it is reducing the hunger.

In general, unless otherwise specified or made clear from the context, virtual reality environments may include any of various different levels of immersion for a user, ranging from complete immersion in computer-generated sensory stimuli to augmented reality environments including both virtual and real-world objects.

As used herein, the terms "real-world," "physical world," "physical space," and variations thereof generally refer to a physical setting separate from computer-generated stimuli. Thus, for example, a physical space may include the location of the patient, for example the dining room.

In certain implementations, virtual reality simulations described herein may show the patient a positive body image while the patient is stimulating their stomach utilizing the methods described above. In one embodiment, this could be a body image of the patient in a more desirable state (such as with reduced body fat). In another embodiment, the virtual reality system encourages movement by the patient. This movement can be physical activity or stretching or any other desired movement.

In one embodiment, the system displays a voluminous meal to the patient, while the patient may actually eating a very small meal or a different meal entirely. This can be done alone, or in combination with stimulating stomach.

In another embodiment, the system may display to the patient pleasurable, relaxed, happy environments while consuming healthy food. For example, the system could detect healthy food through a camera or manual input, and in response display a relaxed or happy environment.

In further embodiments, the pleasurable display is linked to soft gentle movements (by an operator, patient or an automated belt) of the stomach by the magnet stimulating the reward centers in the brain (for example Amygdala). Conversely, the system may display anxiety, fearful, and distressful environments when the patient is consuming unhealthy food. This could be linked to harsher movements of the stomach stimulating pain centers of the brain (incisura).

It will thus be understood that the user(s) of devices, systems, and methods disclosed herein may include a human user seeking an immersive simulated experience (e.g., consuming a desirable meal or displaying a desirable body image). This may include a user looking to experience a simulated meal without consuming the meal in the physical world, e.g., because of a smaller portion size or a different meal being consumed, or to mitigate the risk associated with the meal in question.

It can be appreciated that this feature can also be used as biofeedback without VR. Biofeedback is discussed further in the application.

The present disclosure further provides a machine learning interface. This interface may learn when the patient does a food binge via a wireless connection such as Bluetooth. It can include manual patient input and also use as inputs various patient specifications. These can include patient weight, lab testing, hemoglobic, subjective mood, blood pressure, heart rate. The machine learning algorithm can be programmed to learn what is the best times to stimulate the stomach, and also vary the amount of time based on the individual. For example, it could ask the patient "how much did your hunger drop".

In some implementations, the system may perform a training operation on the machine learning model with patient specifications as defined above. In some implementations, the patient information may include information associated with geographical areas.

The system may separate the historical patient data into a training set, a validation set, a test set, and/or the like. In some implementations, the system may train the machine learning model using, for example, an unsupervised training procedure and based on the historical patient information. For example, the system may perform dimensionality reduction to reduce the historical patient information to a minimum feature set, thereby reducing resources (e.g., processing resources, memory resources, and/or the like) to train the machine learning model, and may apply a classification technique, to the minimum feature set.

Additionally, or alternatively, the system may train the machine learning model using a supervised training procedure that includes receiving input to the machine learning model from a subject matter expert or a group of subject matter experts, such as trained physicians or gastroenterologists, which may reduce an amount of time, an amount of processing resources, and/or the like to train the machine learning model of activity automatability relative to an unsupervised training procedure.

In some implementations, the system uses one or more other machine learning training techniques, such as a neural network technique, a latent semantic indexing technique, and/or the like. For example, the system may perform an artificial neural network processing technique (e.g., using a two-layer feedforward neural network architecture, a three-layer feedforward neural network architecture, and/or the like) to perform pattern recognition with regard to patterns of the historical patient data. In this case, using the artificial neural network processing technique may improve an accuracy of the trained machine learning model generated by the system by being more robust to noisy, imprecise, or incomplete data, and by enabling the system to detect patterns and/or trends undetectable to human analysts (such as doctors) or systems using less complex techniques.

In some implementations, the system may use a logistic regression classification technique to determine a categorical outcome (e.g., that the patient data indicates that certain designated treatment methods are beneficial to the patient). It can be appreciated that the machine learning model may reduce utilization of computing resources relative to manual, linear sorting and analysis of data points, thereby enabling use of thousands of patient data points to train the machine learning model, which may result in a more accurate model than using fewer data points.

Further embodiments of the machine learning interfaces are configured to determine what is the optimal/best behavior for the patient, and may also determine what are the events that makes the patient eat more. The machine learning interface could also encourage other behaviors associated with weight loss or general health. For example, go for a walk. Monitors the patients progress.

The present disclosure further includes embodiments for accountability controls which encourage the patient if he does not comply with the program. In one embodiment, the system becomes locked if a patient do not follow instructions/grocery list/exercise.

The machine can also alert a designated life coach, family member, or physicians that the patient has become non-compliant.

Further embodiments of the present disclosure may provide a computerized reward system for encouraging an patient to participate in a customized weight management program containing some of the embodiments of the present disclosure. In one embodiment, the reward system includes points for buying groceries and other food products. A further embodiment provides a monitoring means for collecting compliance data on an individual participating in the customized weight management program, oversight means for comparing the compliance data with predetermined and/or personalized patient criteria to determine whether or not the individual is compliant, and a reward to be given to the individual who is deemed compliant. For example, compliance may include a predetermined number of times the patient should stimulate their stomach per day. Other rewards could be provided at predetermined goals and/or milestones.

Rewards which are provided to a compliant patient may also be coupons, an electronic reward credited to a debit or credit card, or an electronic reward credited to the individual's account at a participating grocery store or health store, or other participating merchant.

Further accountability features include monitoring patient use and adjusting the time that the machine is usable over time. The time could be increased or decreased based on usage patterns.

Further embodiments provide a community virtual chat room.

Further embodiments may alert the patient a reminder to use the device. The alert could be based on time of day, circadian rhythm of the patient, glucose monitoring event, or the device learning when the patient eats via artificial intelligence techniques described herein. Phone based glucose alerts may also be provided if the glucose of the patient goes down.

Biofeedback teaches the patient how they move the device and how it induces the desired the effect. It can be appreciated that this technique may teach the patient to associate hard food with an alert for a harder pull. Further embodiments of the present disclosure are directed towards providing methods of reconditioning patient behavior and biofeedback, both in conjunction with the intragastric device as well as separately from the intragastric device. Reconditioning or associating a food or eating behavior with an unpleasant or pleasant experience to the patient.

Embodiments of the system are designed to condition or recondition a patient's behavior based on physical sensory inputs to the patient as well as displaying predetermined body images of the patent.

A predetermined positive body image could be a simulated media clip of the patient where in the patient is shown their own body in a desired state, for example with less fat, or with more muscle. In one embodiment, the predetermined positive body image in a simulated media clip of the patient with decreased body fat. In another embodiment, it is a simulated media clip of the patient with increased muscle mass. In a further embodiment, the predetermined positive body image is a simulated media clip of the patient dressed in a clothing of a desired size. The predetermined body images can be generated by questionnaires of the patient including the patient's desired goal weight, desired body fat percentage, and/or desired clothing specifications. A predetermined negative body image could be a simulated media clip of the patient with wherein the patient is shown in an undesirable state. In one embodiment, the predetermined negative body image in a simulated media clip of the patient with increased body fat. In another embodiment, it is a simulated media clip of the patient with decreased muscle mass. states include the patient with increased body fat.

It can be appreciated that the system is designed to provide instructions for body sensory input and associate such inputs with food. Embodiments include instructions to stimulate body parts in response to the VR. In one embodiment, the system includes instructions for negative stimuli to the patient. For example, the system can provide an instruction to immerse a known unpleasant experience, such as immersing a patient's hand in cold water, or a patient's feet in cold water. Other negative stimuli that the instructions may comprise include other uses of cold water, bad smell. The system may also emit negative stimuli directly, including emitting various sounds including high pitch sounds and crying sounds, and electric sounds. In a further embodiment, the system provides a combinations of experiences, wherein the combination can include virtual reality immersion, auditory alerts, and pain inducing instructions to the patient.

The system can provide the reconditioning experiences in conjunction with the internal device. For example, the reconditioning experiences can be displayed at the same time as using the internal device. The reconditioning experience can also continue after a patient has ceased use of the internal device. For example, in one embodiment effective experiences used in conjunction with the intragastric dives can continue even after the device is removed.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

REFERENCES CITED

U.S. Ser. No. 10/265,627B2
U.S. Ser. No. 10/262,290B1
U.S. Pat. No. 6,151,586A

The invention claimed is:

1. A method of stimulating the anterior gastric wall comprising the steps of:
positioning an external magnet in close enough proximity to an intragastric device deployed in a stomach of a patient to create a sufficient magnetic pulling force between the external magnet and the intragastric device to move the intragastric device towards, and impart stimulating force upon an anterior gastric wall;
and providing a visual interface, wherein the visual interface displays a virtual reality reconditioning experience to the patient as part of a treatment, wherein the reconditioning experience is a primary purpose of the treatment together with the intragastric device.

2. The method of claim 1 wherein the virtual reality reconditioning experience further comprises a displaying a body image of the patient.

3. The method of claim 2, wherein the virtual reality reconditioning experience displays the body image to the patient while the stimulating force is imparted on the stomach.

4. The method of claim 3, wherein the body image further comprises a body image of the patient with reduced body fat.

5. The method of claim 1, wherein the virtual reality reconditioning experience further comprises an instruction to perform a stimulus.

6. The method of claim 1, wherein the visual interface displays a meal to the patient while the stimulating force is imparted on the stomach.

7. The method of claim 1, wherein the visual interface displays an environment to the patient while the stimulating force is imparted on the stomach.

8. A system comprising:
a transorally administered intragastric device comprising at least one type of magnetic material, and at least one surface capable of deployment inside of a stomach of a patient, wherein the intragastric device is equipped to impart tactile stimulation upon a stomach wall of the stomach via an external magnet, and wherein a visual interface is configured to display a virtual reality reconditioning experience to the patient, wherein the virtual reality reconditioning further comprises reconditioning instructions to the patient as part of a treatment, wherein the virtual reality reconditioning experience is a primary purpose of the treatment together with the intragastric device.

9. The system of claim 8, wherein the visual interface is configured to display a body image to the patient while the stimulating force is imparted on the stomach.

10. The system of claim 9, wherein the positive body image further comprises a modified body image of the patient.

11. The method of claim 10, wherein the visual interface is configured to alert the patient perform physical activity.

12. The system of claim 8, wherein the visual interface is configured to display a meal to the patient while the stimulating force is imparted on the stomach.

13. The system of claim 8, wherein the visual interface is configured to display an environment to the patient while the stimulating force is imparted on the stomach.

* * * * *